United States Patent
Fiser

(10) Patent No.: US 7,963,943 B2
(45) Date of Patent: Jun. 21, 2011

(54) I.V. CATHETER ASSEMBLY AND NEEDLE SAFETY DEVICE

(75) Inventor: Richard L. Fiser, Wildwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 240 days.

(21) Appl. No.: 12/347,164

(22) Filed: Dec. 31, 2008

(65) Prior Publication Data

US 2009/0131870 A1    May 21, 2009

Related U.S. Application Data

(63) Continuation-in-part of application No. PCT/US2008/077867, filed on Sep. 26, 2008.

(51) Int. Cl.
*A61M 5/00*    (2006.01)
(52) U.S. Cl. ...................................................... 604/110
(58) Field of Classification Search .................. 604/110, 604/162, 164.01, 164.02, 164.03, 164.04, 604/164.05, 164.06, 164.07, 164.08
See application file for complete search history.

(56) References Cited

U.S. PATENT DOCUMENTS

| | | | |
|---|---|---|---|
| 2,623,521 A | 12/1952 | Shaw |
| 3,308,821 A | 3/1967 | Shields |
| 3,610,240 A | 10/1971 | Harautuneian |
| 3,977,400 A | 8/1976 | Moorehead |
| 3,994,287 A | 11/1976 | Turp et al. |
| 4,000,739 A | 1/1977 | Stevens |
| 4,139,009 A | 2/1979 | Alvarez |
| 4,143,853 A | 3/1979 | Abramson |
| 4,160,450 A | 7/1979 | Doherty |
| 4,177,814 A | 12/1979 | Knepshield et al. |
| 4,211,214 A | 7/1980 | Chikashige |
| 4,261,357 A | 4/1981 | Kontos |
| 4,387,879 A | 6/1983 | Tauschinski |
| 4,424,833 A | 1/1984 | Spector et al. |
| 4,430,081 A | 2/1984 | Timmermans |
| 4,436,519 A | 3/1984 | O'Neill |
| 4,447,237 A | 5/1984 | Frisch et al. |
| 4,473,067 A | 9/1984 | Schiff |
| 4,475,548 A | 10/1984 | Muto |
| 4,512,766 A | 4/1985 | Vailancourt |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,634,432 A | 1/1987 | Kocak |
| 4,649,904 A | 3/1987 | Krauter et al. |

(Continued)

FOREIGN PATENT DOCUMENTS

EP    0 750 915 A2    1/1997
(Continued)

*Primary Examiner* — Nicholas D Lucchesi
*Assistant Examiner* — Aarti B Berdichevsky
(74) *Attorney, Agent, or Firm* — Lisa E. Winsor, Esq.

(57) ABSTRACT

An I.V. catheter assembly and needle safety device are disclosed which allow for the safe removal of a needle from a catheter assembly. The safety device includes a locking assembly which includes lock housing a rotatable locking member and a locking clip. The needle and the locking member are configured such that withdrawal of the needle from the catheter assembly effects rotation of the locking member. The locking clip is positioned and configured to obstruct rotation of the locking member after the needle has been retracted within the housing to obstruct re-advancement of the needle.

9 Claims, 20 Drawing Sheets

U.S. PATENT DOCUMENTS

| | | |
|---|---|---|
| 4,655,752 A | 4/1987 | Honkanen et al. |
| 4,673,393 A | 6/1987 | Suzuki et al. |
| 4,705,511 A | 11/1987 | Kocak |
| 4,715,360 A | 12/1987 | Akui et al. |
| 4,722,725 A | 2/1988 | Sawyer et al. |
| 4,725,267 A | 2/1988 | Vaillancourt |
| 4,735,619 A | 4/1988 | Sperry et al. |
| 4,747,831 A | 5/1988 | Kulli |
| 4,758,225 A | 7/1988 | Cox et al. |
| 4,762,516 A | 8/1988 | Luther et al. |
| 4,781,692 A | 11/1988 | Jagger et al. |
| 4,781,693 A | 11/1988 | Martinez et al. |
| 4,795,432 A | 1/1989 | Karczmer |
| 4,798,594 A | 1/1989 | Hillstead |
| 4,809,679 A | 3/1989 | Shimonaka et al. |
| 4,817,631 A | 4/1989 | Schnepp-Pesch et al. |
| 4,846,809 A | 7/1989 | Sims |
| 4,857,062 A | 8/1989 | Russell |
| 4,874,377 A | 10/1989 | Newgard et al. |
| 4,895,346 A | 1/1990 | Steigerwald |
| 4,895,565 A | 1/1990 | Hillstead |
| 4,900,307 A | 2/1990 | Kulli |
| 4,904,242 A | 2/1990 | Kulli |
| 4,909,793 A | 3/1990 | Vining et al. |
| 4,909,798 A | 3/1990 | Fleischhacker et al. |
| 4,911,706 A | 3/1990 | Levitt |
| 4,917,668 A | 4/1990 | Haindl |
| 4,927,414 A | 5/1990 | Kulli |
| 4,929,234 A | 5/1990 | Chen |
| 4,931,044 A | 6/1990 | Beiter |
| 4,932,633 A | 6/1990 | Johnson et al. |
| 4,935,010 A | 6/1990 | Cox et al. |
| 4,944,725 A | 7/1990 | McDonald |
| 4,950,250 A | 8/1990 | Haber et al. |
| 4,950,257 A | 8/1990 | Hibbs et al. |
| 4,952,207 A | 8/1990 | Lemieux |
| 4,955,866 A | 9/1990 | Corey |
| 4,960,412 A | 10/1990 | Fink |
| 4,964,854 A | 10/1990 | Luther |
| 4,966,587 A | 10/1990 | Baumgart |
| 4,978,344 A | 12/1990 | Dombrowski et al. |
| 4,994,041 A | 2/1991 | Dombrowski et al. |
| 5,000,745 A | 3/1991 | Guest et al. |
| 5,013,304 A | 5/1991 | Russell et al. |
| 5,049,136 A | 9/1991 | Johnson |
| 5,051,109 A | 9/1991 | Simon |
| 5,053,017 A | 10/1991 | Chamuel |
| 5,085,645 A | 2/1992 | Purdy et al. |
| 5,085,648 A | 2/1992 | Purdy et al. |
| 5,108,374 A | 4/1992 | Lemieux |
| 5,126,090 A | 6/1992 | Egolf et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,183,468 A | 2/1993 | McLees |
| 5,195,983 A | 3/1993 | Boese |
| 5,215,528 A | 6/1993 | Purdy et al. |
| 5,322,517 A | 6/1994 | Sircom et al. |
| 5,322,518 A | 6/1994 | Schneider et al. |
| 5,328,482 A | 7/1994 | Sircom et al. |
| 5,334,158 A | 8/1994 | McLees |
| 5,338,311 A | 8/1994 | Mahurkar |
| 5,344,408 A | 9/1994 | Partika |
| 5,348,544 A | 9/1994 | Sweeney et al. |
| 5,364,387 A | 11/1994 | Sweeney |
| 5,370,623 A | 12/1994 | Kreamer |
| 5,390,898 A | 2/1995 | Smedley et al. |
| 5,409,461 A | 4/1995 | Steinman |
| 5,417,659 A | 5/1995 | Gaba |
| 5,419,766 A | 5/1995 | Chang et al. |
| 5,423,766 A | 6/1995 | Di Cesare |
| 5,425,884 A | 6/1995 | Botz |
| 5,466,223 A | 11/1995 | Bressler et al. |
| 5,514,100 A | 5/1996 | Mahurkar |
| 5,535,771 A | 7/1996 | Purdy et al. |
| 5,555,908 A | 9/1996 | Edwards et al. |
| 5,558,651 A | 9/1996 | Crawford et al. |
| 5,562,633 A | 10/1996 | Wozencroft |
| 5,572,516 A | 11/1996 | Miya et al. |
| 5,584,809 A | 12/1996 | Gaba |
| 5,584,810 A | 12/1996 | Brimhall |
| 5,584,818 A | 12/1996 | Morrison |
| 5,599,310 A | 2/1997 | Bogert |
| 5,601,536 A | 2/1997 | Crawford et al. |
| 5,672,161 A | 9/1997 | Allen et al. |
| 5,685,862 A | 11/1997 | Mahurkar |
| 5,690,619 A | 11/1997 | Erskine |
| 5,693,022 A | 12/1997 | Haynes |
| 5,700,249 A | 12/1997 | Jenkins |
| 5,702,369 A | 12/1997 | Mercereau |
| 5,718,688 A | 2/1998 | Wozencroft |
| 5,735,827 A | 4/1998 | Adwers et al. |
| 5,738,144 A | 4/1998 | Rogers |
| 5,788,215 A | 8/1998 | Ryan |
| 5,806,551 A | 9/1998 | Meloul et al. |
| 5,806,831 A | 9/1998 | Paradis |
| 5,814,098 A | 9/1998 | Hinnenkamp et al. |
| 5,817,069 A | 10/1998 | Arnett |
| 5,836,921 A | 11/1998 | Mahurkar |
| 5,853,393 A | 12/1998 | Bogert |
| 5,865,806 A | 2/1999 | Howell |
| 5,879,338 A | 3/1999 | Mahurkar |
| 5,891,105 A | 4/1999 | Mahurkar |
| 5,893,845 A | 4/1999 | Newby et al. |
| 5,911,705 A | 6/1999 | Howell |
| 5,928,162 A | 7/1999 | Giurtino et al. |
| 5,935,109 A | 8/1999 | Donnan |
| 5,947,930 A | 9/1999 | Schwemberger et al. |
| 5,954,313 A | 9/1999 | Ryan |
| 5,954,698 A | 9/1999 | Pike |
| 5,957,887 A | 9/1999 | Österlind et al. |
| 5,957,892 A | 9/1999 | Thorne |
| 5,967,490 A | 10/1999 | Pike |
| 5,967,698 A | 10/1999 | Pascoe |
| 5,980,488 A | 11/1999 | Thorne |
| 5,989,229 A | 11/1999 | Chiappetta |
| 6,001,080 A | 12/1999 | Kuracina et al. |
| 6,004,294 A | 12/1999 | Brimhall et al. |
| 6,068,011 A | 5/2000 | Paradis |
| 6,068,617 A | 5/2000 | Richmond |
| RE36,885 E | 9/2000 | Blecher et al. |
| 6,117,108 A | 9/2000 | Woehr et al. |
| 6,117,112 A | 9/2000 | Mahurkar |
| 6,132,401 A | 10/2000 | Van Der Meyden et al. |
| 6,171,284 B1 | 1/2001 | Kao et al. |
| 6,221,047 B1 | 4/2001 | Greene et al. |
| 6,224,569 B1 | 5/2001 | Brimhall |
| 6,280,399 B1 | 8/2001 | Rossin et al. |
| 6,280,401 B1 | 8/2001 | Mahurkar |
| 6,280,419 B1 | 8/2001 | Vojtasek |
| 6,287,278 B1 | 9/2001 | Woehr et al. |
| 6,322,537 B1 | 11/2001 | Chang |
| 6,346,094 B2 | 2/2002 | West et al. |
| 6,361,525 B2 | 3/2002 | Capes et al. |
| 6,379,333 B1 | 4/2002 | Brimhall et al. |
| 6,406,459 B1 | 6/2002 | Allmon |
| 6,409,701 B1 | 6/2002 | Cohn et al. |
| 6,443,927 B1 | 9/2002 | Cook |
| 6,485,473 B1 | 11/2002 | Lynn |
| 6,500,129 B1 | 12/2002 | Mahurkar |
| 6,537,259 B1 | 3/2003 | Niermann |
| 6,551,287 B2 | 4/2003 | Hollister et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,638,254 B2 | 10/2003 | Nakagami |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford et al. |
| 6,682,510 B2 | 1/2004 | Niermann |
| 6,689,102 B2 | 2/2004 | Greene |
| 6,692,471 B2 | 2/2004 | Boudreaux |
| 6,699,221 B2 | 3/2004 | Vaillancourt |

| | | |
|---|---|---|
| 6,740,063 B2 | 5/2004 | Lynn |
| 6,749,588 B1 | 6/2004 | Howell et al. |
| 6,671,704 B1 | 7/2004 | Crawford |
| 6,761,706 B2 | 7/2004 | Vaillancourt |
| 6,767,336 B1 | 7/2004 | Kaplan |
| 6,796,962 B2 | 9/2004 | Ferguson et al. |
| 6,802,490 B2 | 10/2004 | Leinsing et al. |
| 6,832,992 B2 | 12/2004 | Wilkinson |
| 6,855,128 B2 | 2/2005 | Swenson |
| 6,855,130 B2 | 2/2005 | Saulenas et al. |
| 6,902,546 B2 | 6/2005 | Ferguson |
| 6,916,311 B2 | 7/2005 | Vojtasek |
| 6,936,036 B2 | 8/2005 | Wilkinson et al. |
| 6,984,213 B2 | 1/2006 | Horner et al. |
| 7,004,927 B2 | 2/2006 | Ferguson et al. |
| 7,828,774 B2 * | 11/2010 | Harding et al. .......... 604/164.08 |
| 2002/0151850 A1 | 10/2002 | Ferguson et al. |
| 2002/0193745 A1 | 12/2002 | Ferguson |
| 2003/0060769 A1 * | 3/2003 | Rhad et al. ............... 604/164.07 |
| 2003/0144627 A1 | 7/2003 | Woehr et al. |
| 2003/0195471 A1 | 10/2003 | Woehr et al. |
| 2003/0220617 A1 | 11/2003 | Dickerson |
| 2004/0078003 A1 | 4/2004 | Smith et al. |
| 2004/0092889 A1 | 5/2004 | Ferguson et al. |
| 2004/0133167 A1 | 7/2004 | Ferguson et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0059937 A1 | 3/2005 | Ferguson |
| 2005/0070855 A1 | 3/2005 | Ferguson et al. |
| 2005/0096592 A1 | 5/2005 | Carlyon et al. |
| 2006/0173439 A1 * | 8/2006 | Thorne et al. ................. 604/506 |
| 2007/0112305 A1 | 5/2007 | Brimhall |

FOREIGN PATENT DOCUMENTS

| | | |
|---|---|---|
| EP | 0 750 915 A3 | 1/1997 |
| EP | 1 112 754 B1 | 2/2005 |
| WO | WO 96/22800 A1 | 8/1996 |
| WO | WO 97/42989 A1 | 11/1997 |
| WO | WO 2005/042073 A1 | 5/2005 |

* cited by examiner

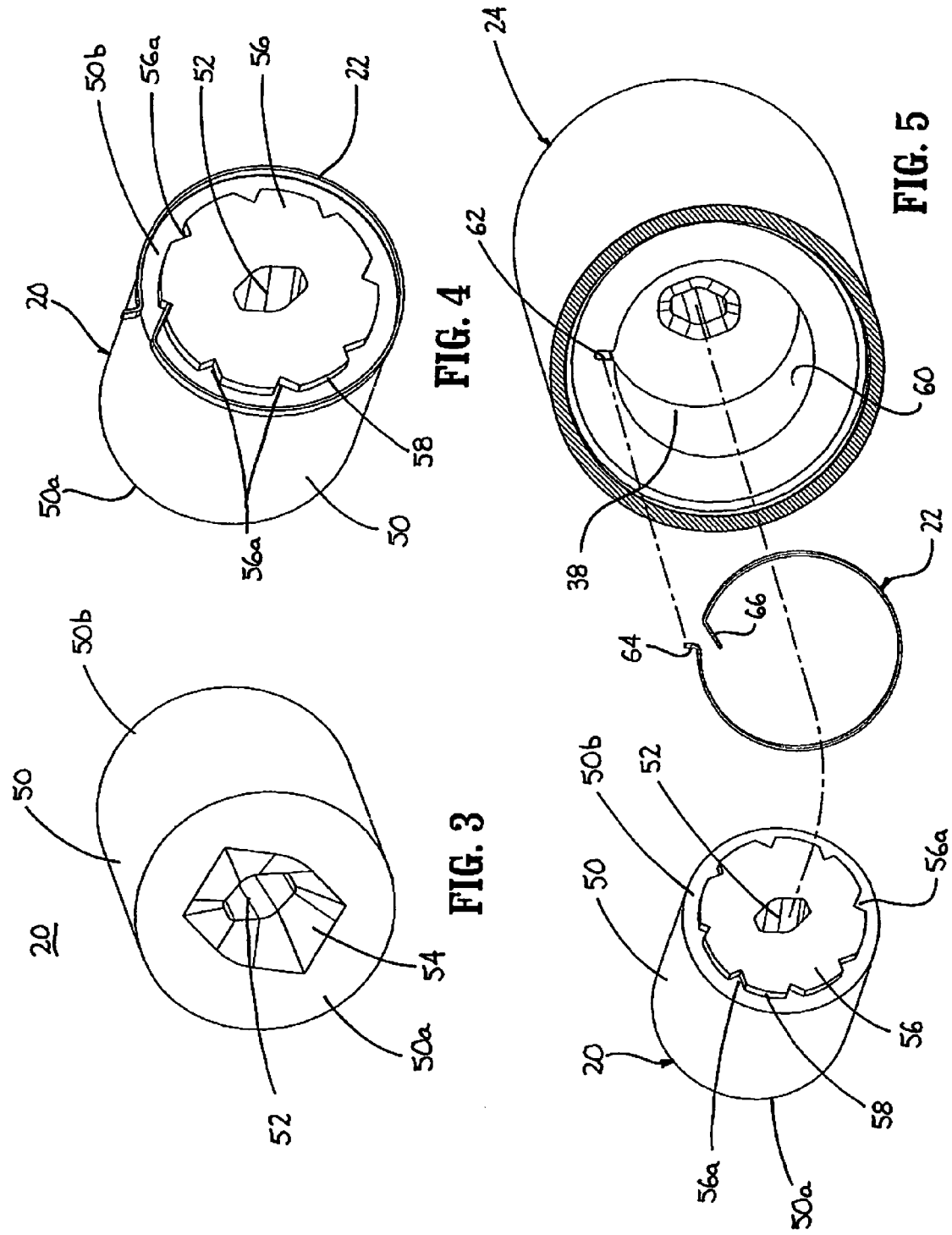

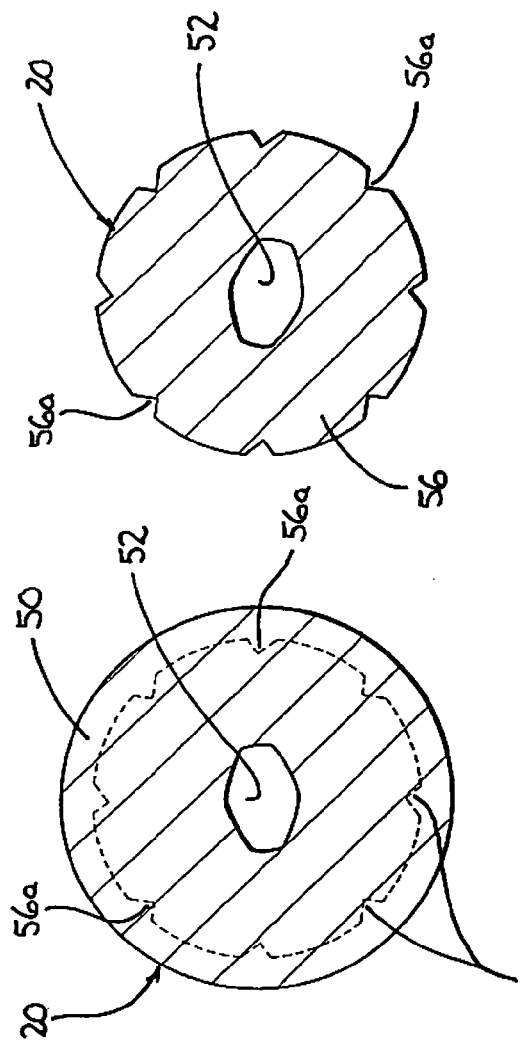
FIG. 6
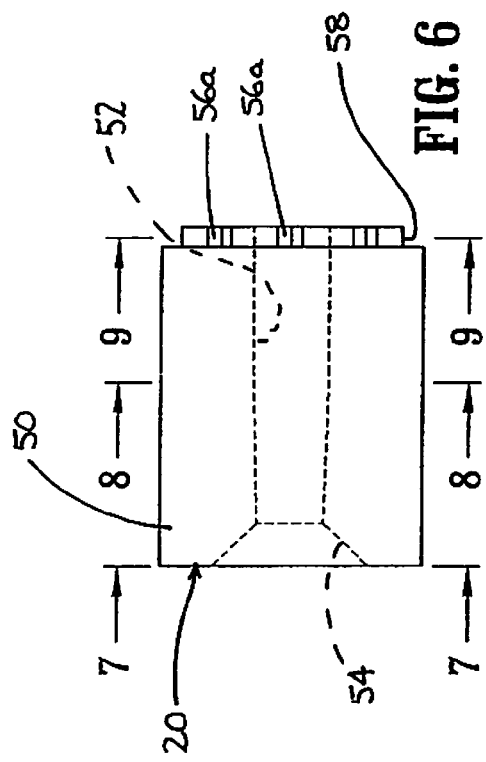
FIG. 8
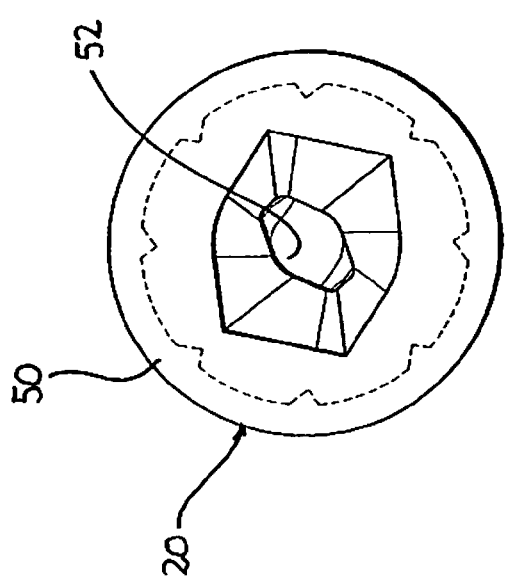
FIG. 9
FIG. 7

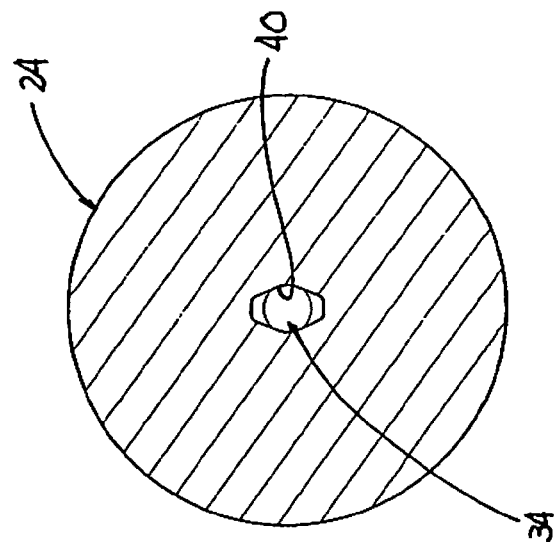
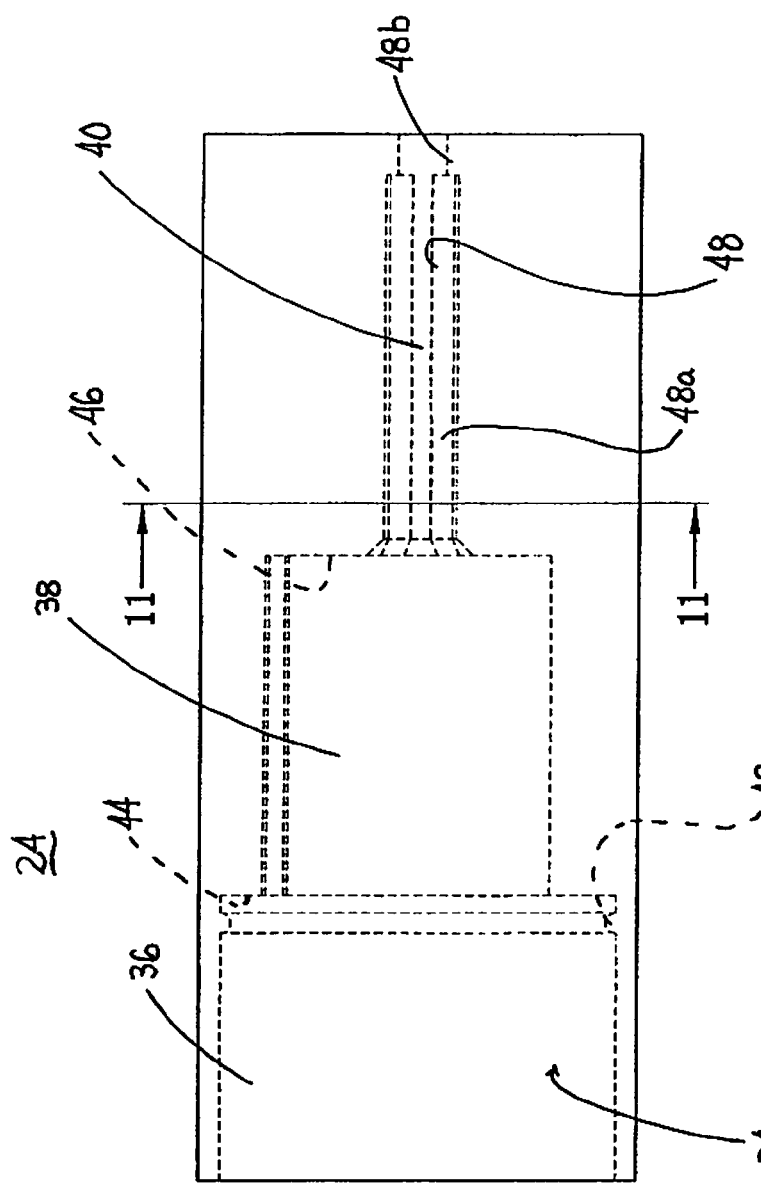
FIG. 11
FIG. 10

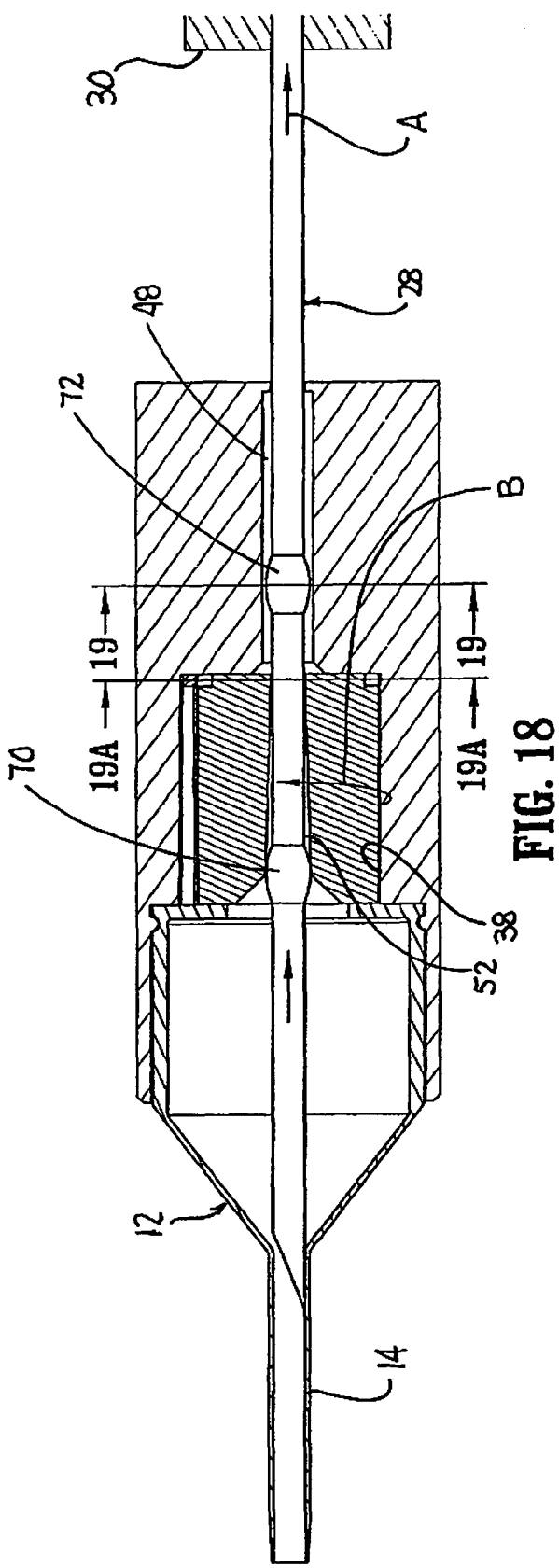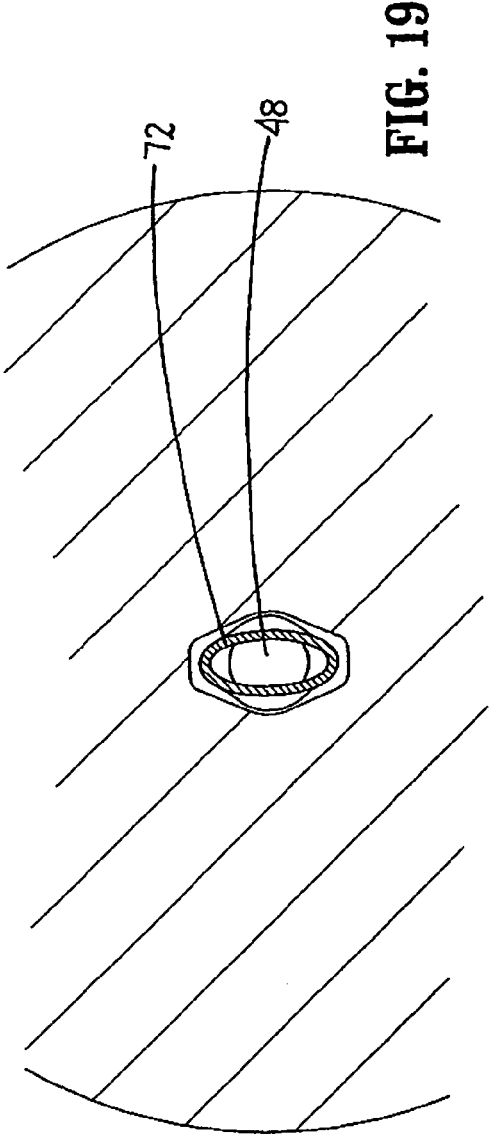
FIG. 18
FIG. 19

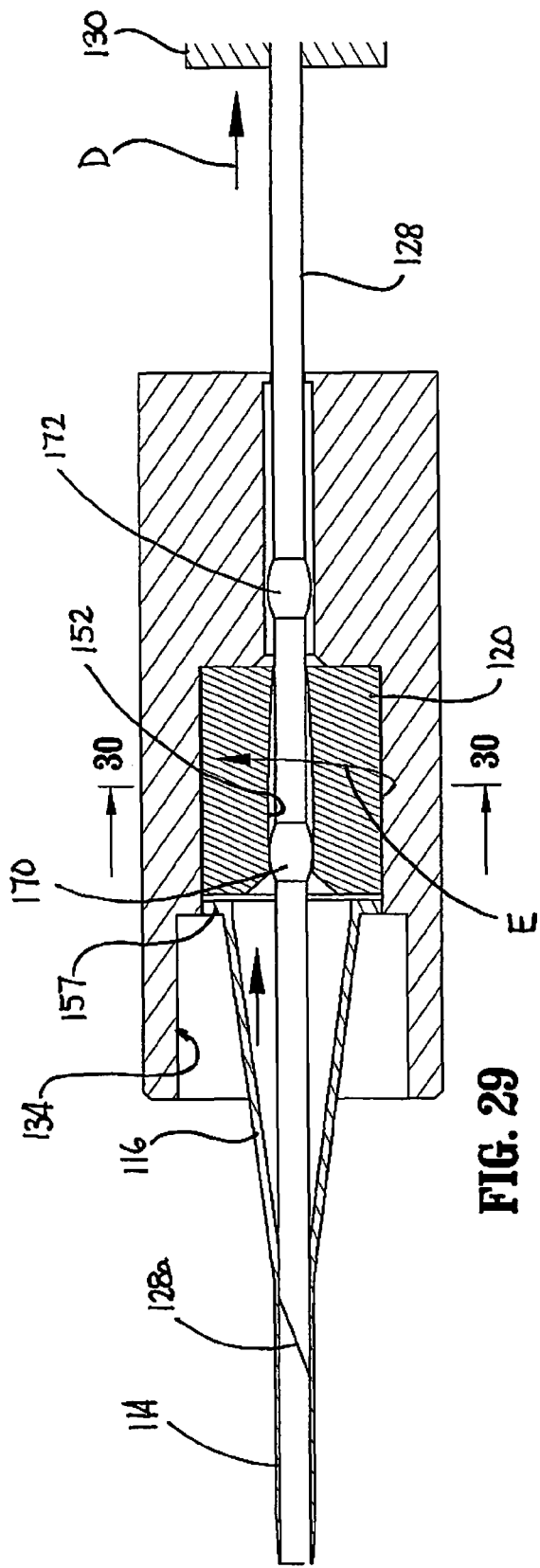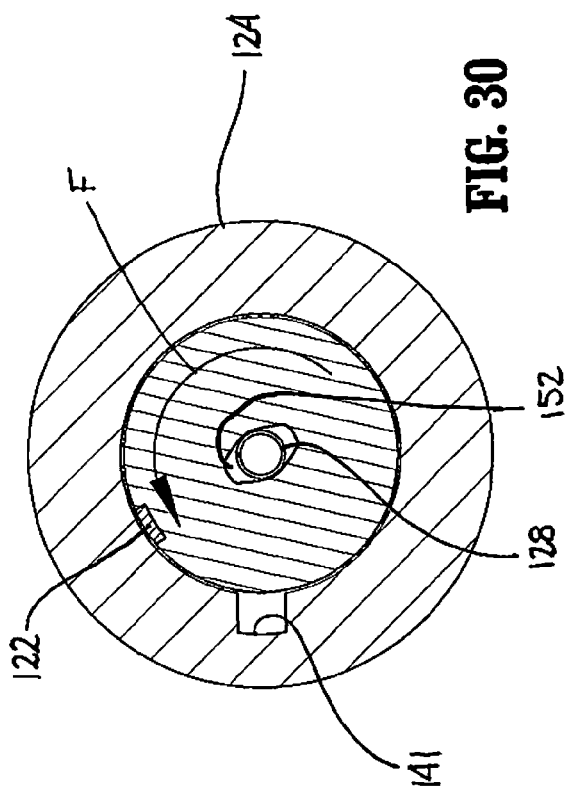
FIG. 29
FIG. 30

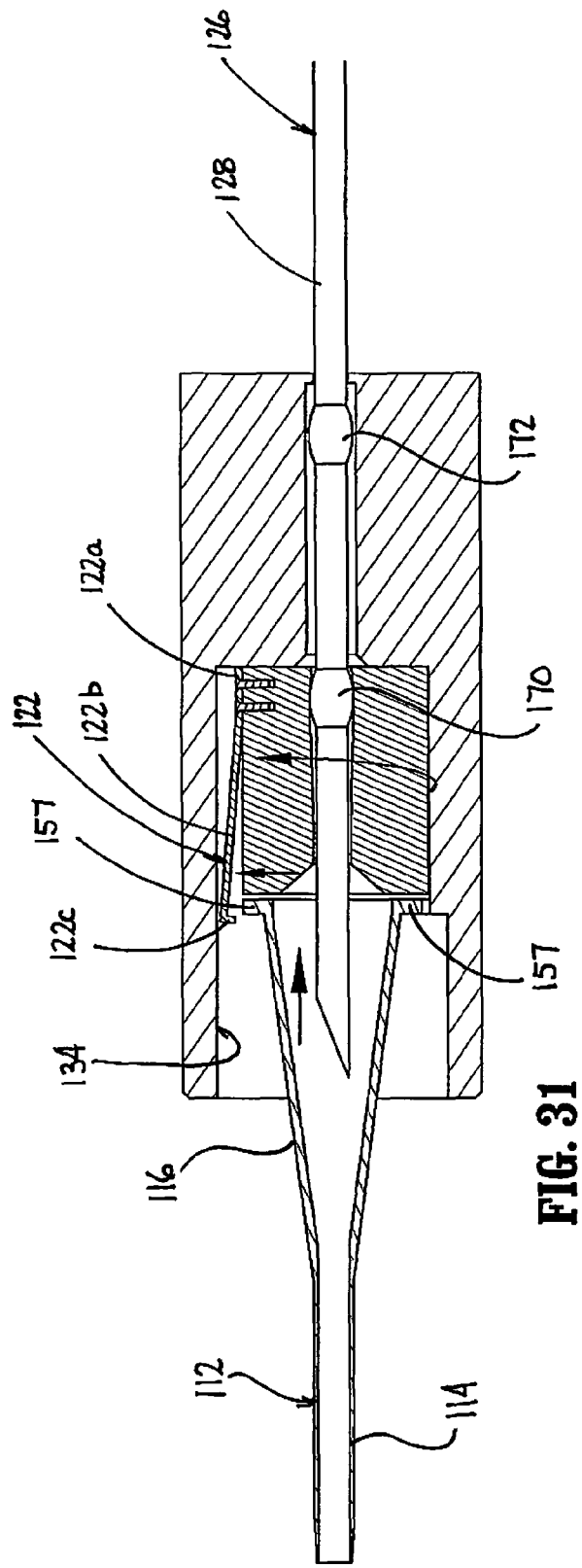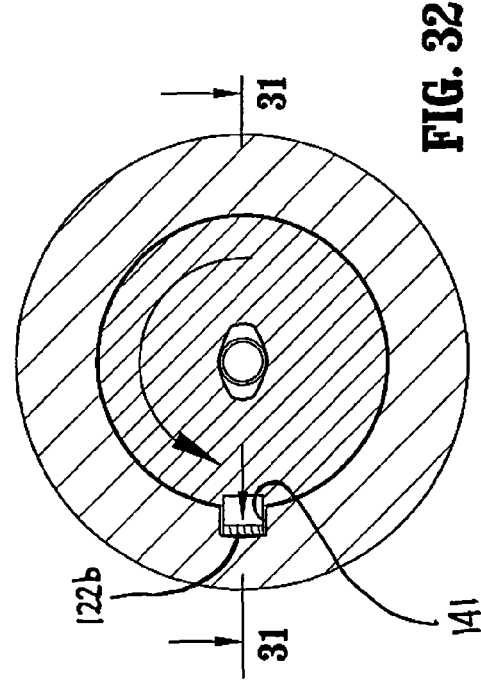
FIG. 31
FIG. 32

I.V. CATHETER ASSEMBLY AND NEEDLE SAFETY DEVICE

CROSS REFERENCE TO RELATED APPLICATIONS

This application claims priority to PCT International Application PCT/US08/77867 filed on Sep. 26, 2008 which claims priority to U.S. provisional application Ser. No. 60/995,540 filed Sep. 27, 2007.

BACKGROUND

1. Technical Field

The present disclosure relates to an intravenous or I.V. catheter device. More particularly the present disclosure relates to a safety device for shielding the tip of a needle used for placement of an I.V. catheter device in the vasculature of a patient.

2. Background of Related Art

Safety devices for shielding needles of medical devices are well known in the art. Such devices minimize the risks associated with inadvertent needle stick injuries which subject doctors, nurses and medical personnel to exposure to HIV, hepatitis and other serious blood-borne pathogens.

Passively activated safety devices are also known in the art. Typically, such devices actuate the safety device in response to normal usage of a medical device with which the safety device is associated e.g., removal of a needle from an I.V. catheter.

Intravenous catheter devices are also known in the art and typically include a catheter which is dimensioned to be positioned into a patient's vasculature and a needle having a sharp tip which is provided to facilitate placement of the catheter into the patient's vasculature. In use, after placement of the catheter, the needle is separated from the catheter and disposed of safely. One problem associated with the use of I.V. catheters is the risk to medical personnel of needle stick injury during disposal of the needle after separation of the needle from the catheter. To minimize the risks to medical personnel during needle disposal, the use of spring clips which attach to the needle and shield the needle tip has become well known. Such spring clips, although somewhat effective, have been known to become disengaged from the needle, thus rendering medical personnel susceptible to needle stick injury.

Accordingly, a continuing need exists in the medical arts for an I.V. catheter assembly which includes structure for safely and irreversibly shielding a needle tip of a needle after the needle has been separated from the catheter.

SUMMARY

An IV catheter assembly and needle safety device are disclosed. The IV catheter assembly comprises a catheter and a catheter hub. The needle safety device comprises a lock assembly including a housing, a locking member and a stop member. The housing defines a throughbore and has a distal end configured to engage a proximal end of the catheter hub. The locking member also defines a throughbore and is rotatably supported within the housing throughbore. The stop member is positioned to engage the locking member to substantially prevent rotation of the locking member in a first direction. A needle is provided which has a distal tip. The needle is positioned through the housing throughbore, the locking member throughbore and the catheter when the needle is in an advanced position such that the distal tip of the needle projects from a distal end of the catheter. The needle is movable from the advanced position to a retracted position within the housing and has a first portion movable through the locking member throughbore. The first portion is configured to effect rotation of the locking member in a second direction during movement of the needle toward the retracted position and effect rotation of the locking member in the first direction during movement of the needle towards the advanced position. The distal tip of the needle can be sharpened to pierce tissue.

In one embodiment, the catheter hub is configured to releasably engage the housing of the lock assembly. One of the throughbore of the housing and the catheter hub may define an annular recess and the other of the throughbore of the housing and the catheter hub may include an annular rib configured to be releasably received within the annular recess.

In one embodiment, the first portion of the needle includes a non-circular portion, and the locking member throughbore has a non-circular shape which rotates about its longitudinal axis such that the locking member throughbore receives the first portion of the needle in a screw-like manner. The needle may include a pair of spaced non-circular portions.

In one embodiment, the lock assembly includes a locking clip and the stop member is formed on one end of the locking clip. The locking clip may be rotatably fixed within the housing throughbore. Further, the locking member may be substantially cylindrical and rotatably supported within the housing throughbore adjacent the locking clip. In one embodiment, the locking member includes a stepped portion defining a circular track having at least one cutout positioned to receive the stop member. The circular track may include a series of cutouts such that the stop member and cutouts are in ratcheting engagement.

A needle safety device is also disclosed which includes a housing, a locking member and a stop member. The housing and the locking member each define a throughbore and the locking member is rotatably supported within the housing throughbore. The stop member is positioned to engage the locking member to substantially prevent rotation of the locking member in a first direction. In one embodiment, the locking member throughbore has a screw-like configuration which is dimensioned to slidably receive a needle such that movement of the needle in relation to the locking member effects rotation of the locking member.

The safety device may also include a locking clip. The stop member may be formed on one end of the locking clip. In one embodiment, the locking clip is rotatably fixed within the housing throughbore. The locking member may be substantially cylindrical and rotatably supported within the housing throughbore adjacent the locking clip. In one embodiment, the locking member includes a stepped portion defining a circular track having at least one cutout positioned to receive the stop member. The circular track may include a series of cutouts such that the stop member and cutouts are in ratcheting engagement.

BRIEF DESCRIPTION OF THE DRAWINGS

Various embodiments of the presently disclosed I.V. catheter assembly and needle safety device are disclosed herein with reference to the drawings, wherein:

FIG. 3 is a perspective view from the distal end of the locking member of the lock assembly of the I.V. catheter assembly and needle safety device;

FIG. 4 is a perspective view from the proximal end of the locking member of the lock assembly of the safety device shown in FIG. 4 with the locking clip supported thereon;

FIG. 5 is a perspective cross-sectional view with parts separated of the lock assembly of the I.V. catheter assembly and needle safety device shown in FIG. 1;

FIG. 6 is a side view of the locking member shown in FIG. 3 showing the locking channel in phantom;

FIG. 7 is a front end elevational view of the locking member shown in FIG. 3;

FIG. 8 is a cross-sectional view of the locking member taken along section lines 8-8 of FIG. 6;

FIG. 9 is a cross-sectional view of the locking member taken along section lines 9-9 of FIG. 6;

FIG. 10 is a side view of the housing of the locking assembly shown in FIG. 5 with the housing throughbore shown in phantom;

FIG. 11 is a cross-sectional view of the housing of the locking assembly taken along section lines 11-11 of FIG. 10;

FIG. 18 is a side cross-sectional view of the I.V. catheter assembly and needle safety device shown in FIG. 1 with the needle partially retracted;

FIG. 19 is a cross-sectional view taken along section lines 19-19 of FIG. 18;

FIG. 28A is a cross-sectional view of the presently disclosed I.V. catheter assembly and needle safety device taken along section lines 28A-28A of FIG. 27;

FIG. 28B is a cross-sectional view of the presently disclosed I.V. catheter assembly and needle safety device taken along section lines 28B-28B of FIG. 28A;

FIG. 29 is a side cross-sectional view of the presently disclosed I.V. catheter assembly and needle safety device shown in FIG. 25 with the needle partially retracted;

FIG. 30 is a cross-sectional view taken along section lines 30-30 of FIG. 29;

FIG. 31 is a side cross-sectional view of the I.V. catheter assembly and needle safety device shown in FIG. 25 with the needle fully retracted;

FIG. 32 is cross-sectional view of the presently disclosed I.V. catheter assembly and needle safety device shown in FIG. 31 taken through the hub and the lock housing;

DETAILED DESCRIPTION OF THE EMBODIMENTS

Figure 1:
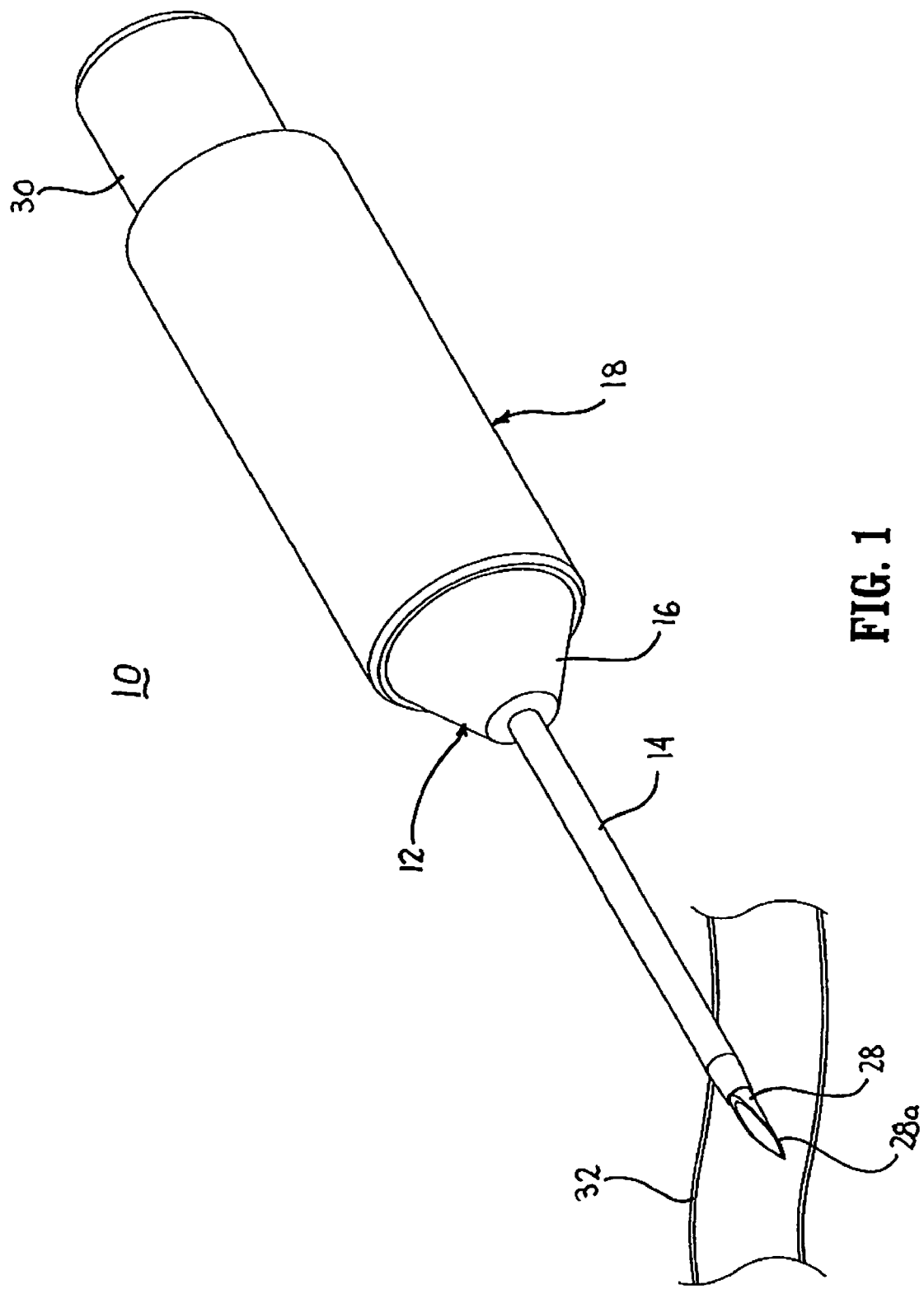
FIG. 1 is a side perspective view of one embodiment of the presently disclosed I.V. catheter assembly and needle safety device with the needle tip of the needle projecting from the distal end of the catheter and the catheter inserted into a vein.

Embodiments of the presently disclosed I.V. catheter assembly and needle safety device will now be described in detail with reference to the drawings wherein like reference numerals designate identical or corresponding elements in each of the several views. In this description, the term proximally is generally used to indicate relative nearness of a referenced item to a user of the device and the term distal is used to indicate relative remoteness of a referenced item to a user of the device.

Figure 2:
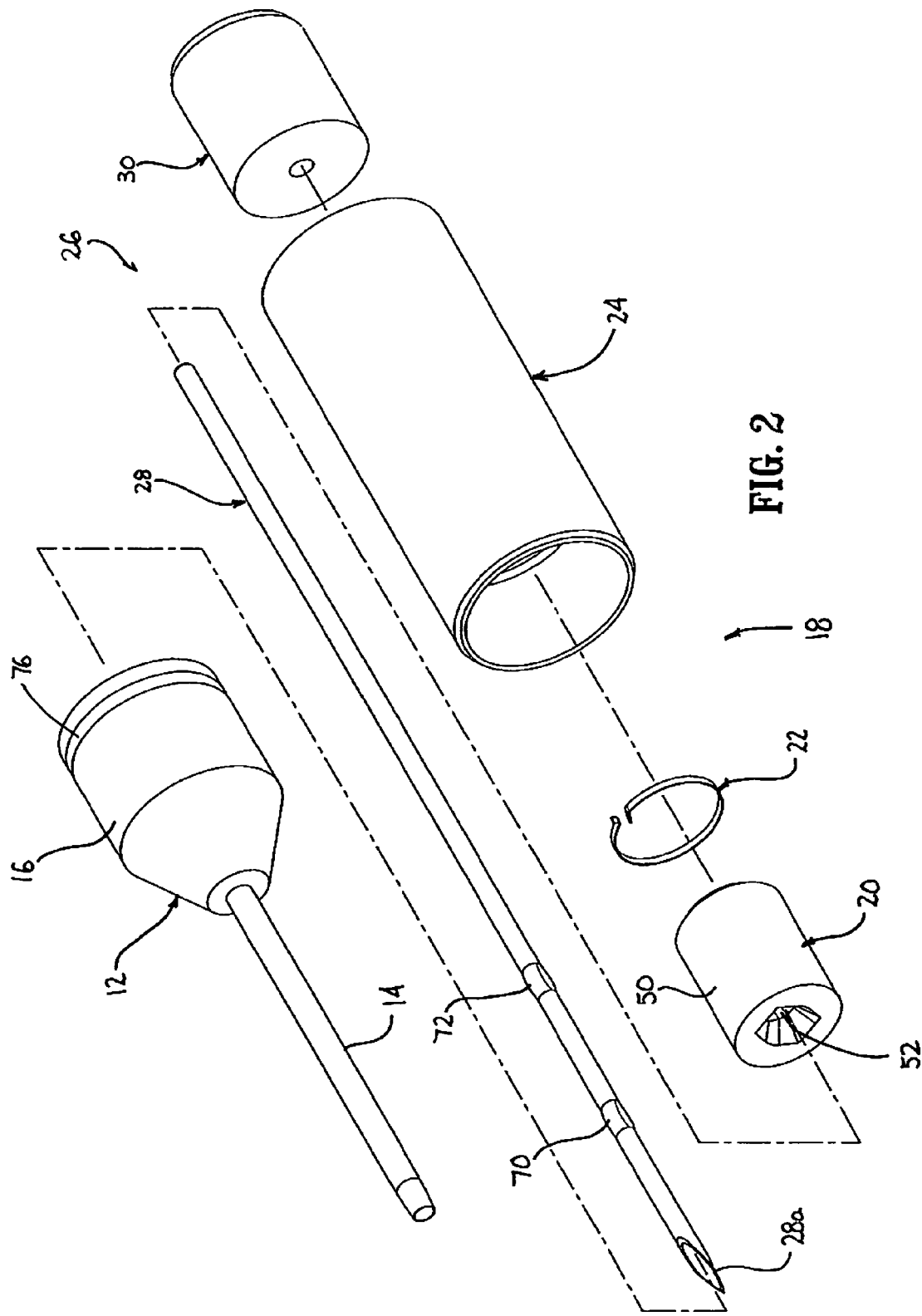
FIG. 2 is a side perspective view of the I.V. catheter assembly and needle safety device shown in FIG. 1 with parts separated.
Figure 12:
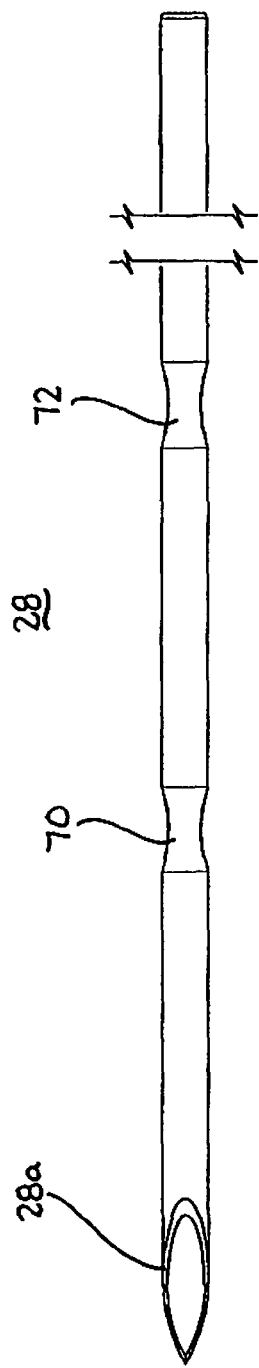
FIG. 12 is a top view of the needle of the I.V. catheter assembly and needle safety device shown in FIG. 2.
Figure 13:
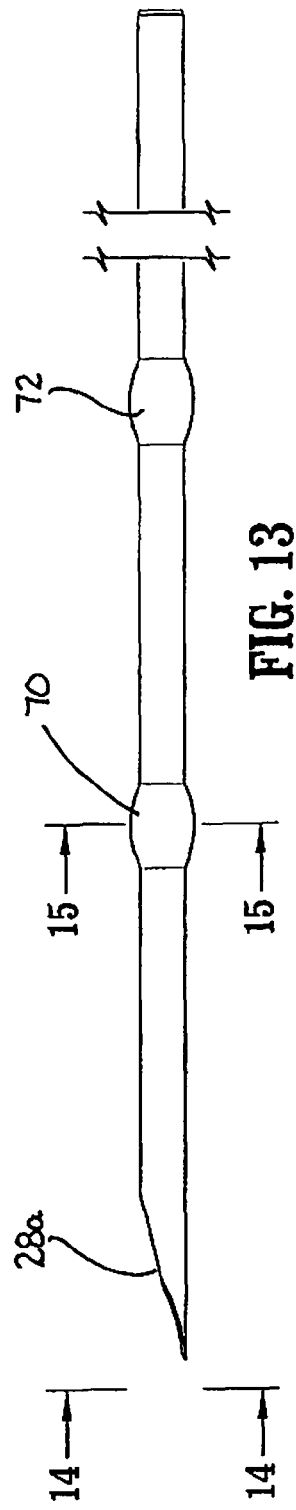
FIG. 13 is a side view of the needle of the I.V. catheter assembly and needle safety device shown in FIG. 12.
Figure 15:
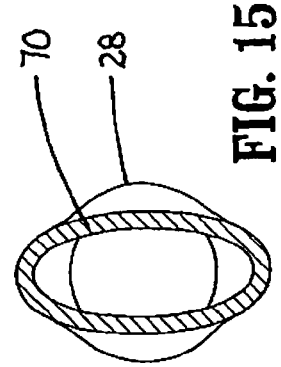
FIG. 15 is a cross-sectional view taken along section lines 15-15 of FIG. 13.
Figure 14:
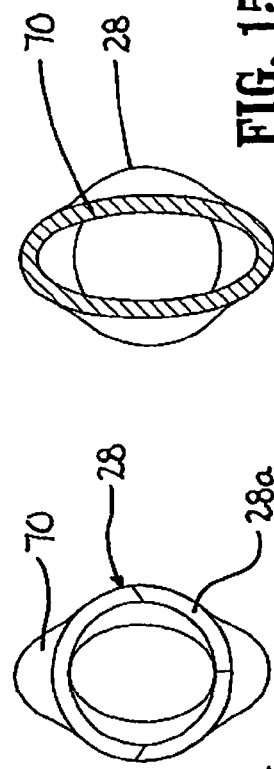
FIG. 14 is an elevational view from the distal end of the needle shown in FIG. 13.

FIGS. 1-22 illustrate one embodiment of the presently disclosed I.V. catheter assembly and needle safety device ("the device") shown generally as 10. Referring to FIGS. 1 and 2, the device 10 includes a catheter assembly 12 including a catheter 14 and a catheter hub 16, a safety device or lock assembly 18 including a rotatable locking member 20, a locking clip 22 and lock housing 24, and a needle assembly 26 including an elongated needle 28 and a needle hub 30. As will be described in further detail below, needle 28 is positioned through lock assembly 18 and catheter assembly 12 such that in its extended position, a sharpened, tapered tip 28a of needle 28 extends from the distal end of catheter 14. As is known in the art, sharpened tip 28a facilitates insertion of needle 28 and catheter 14 into the vasculature, e.g., vein 32 (FIG. 1), of a patient.

Figure 16:
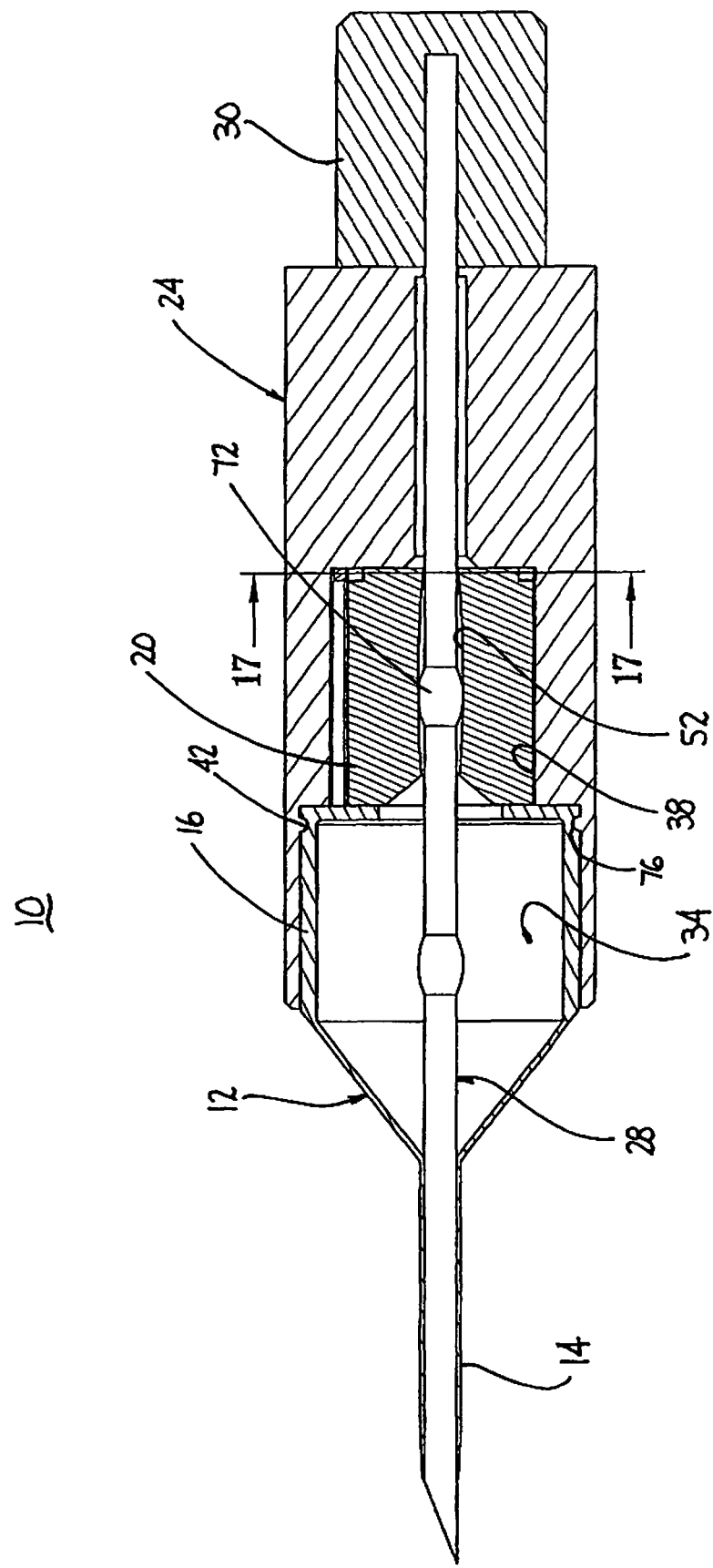
FIG. 16 is a side cross-sectional view of the I.V. catheter assembly and needle safety device shown in FIG. 1 with the needle in its extended position.

Referring to FIGS. 2, 10 and 11, lock housing 24 defines a stepped bore 34 having a substantially cylindrical distal portion 36, a substantially cylindrical central portion 38 and a proximal portion 40. Distal portion 36 is dimensioned to receive the proximal end of catheter hub 16. In one embodiment, an annular rib 42 is formed about an inner wall of housing 24 in distal portion 36 and functions to releasably engage catheter hub 16 as will be described in further detail below. A first shoulder portion or step 44 is positioned between distal portion 36 and central portion 38 of stepped bore 34. Step 44 engages the proximal end of catheter hub 16 when catheter assembly 12 is secured to housing 24 (FIG. 16). Central portion 38 of stepped bore 34 is dimensioned to rotatably receive locking member 20 of lock assembly 18. A second shoulder portion or step 46 is positioned between central portion 38 and proximal portion 40 of stepped bore 34. Step 46 engages the proximal end of locking member 20 when member 20 is positioned in central portion 38 of bore 34. Proximal portion 40 includes a throughbore 48. At least a portion 48a of throughbore 48 has a non-circular shape, e.g., truncated oval shape. The proximal end of throughbore 48 also includes an inwardly extending flange 48b of reduced diameter which will be discussed in further detail below. Non-circular portion 48a functions to prevent rotation of needle 28 in relation to housing 24 and to lock needle 28 in a retracted position in relation to housing 24 as will be described in detail below.

Referring to FIGS. 2-9, locking member 20 has a substantially cylindrical body 50 defining a non-circular throughbore 52, e.g., truncated oval shape, which is rotated or twisted along its longitudinal axis, e.g. partial helix. See FIGS. 6-9. A distal end 50a of locking member 20 includes a channeling surface 54 which will be discussed in further detail below. A proximal end 50b of locking member 20 includes a stepped portion 56 with a series of cutouts 56a formed along a circular track 58 formed about stepped portion 56. An inner wall 60 defining central portion 38 of stepped bore 34 includes a cutout 62. Locking clip 22 includes a substantially circular member formed of a spring material including a first end having an outwardly extending finger 64 and a second end having an inwardly angled stop member 66. Finger 64 is configured and dimensioned to be received within cutout 62 to rotatably fix locking clip 22 about proximal end 50b of locking member 20. When finger 64 is positioned within cutout 62, clip 22 is non-rotatably secured to housing 24 and stop member 66 is positioned to ride over circular track 58 of stepped portion 56 of locking member 20 as locking member 20 rotates within central portion 38 of stepped bore 34. As locking member 20 rotates in relation to clip 22 and housing 24, stop member 66 ratchets into and out of cutouts 56a. Because of the angled faces defining cutouts 56a and the angle of stop member 66, locking clip 22 will permit rotation of locking member 20 in a first direction but prevent rotation of locking member 20 in the opposite direction.

Referring to FIGS. 2 and 12-15, as discussed above, needle assembly 26 includes a needle hub 30 and a needle 28 having a sharpened tip 28a. Sharpened tip 28a defines a beveled surface configured to pierce body tissue to access vasculature of a patient. Needle 30 further includes first and second non-circular portions 70 and 72 which are configured and dimensioned to be slidably received within throughbore 52 of locking member 20 and within non-circular portion 48a of throughbore 48 of housing 24. Needle hub 30 is secured to the proximal end of needle 28 and provides a gripping surface to facilitate removal of needle 28 from catheter assembly 12. Needle hub 30 can be secured to needle 28 using any known fastening technique including adhesion, crimping, press-fitting.

Figure 17:
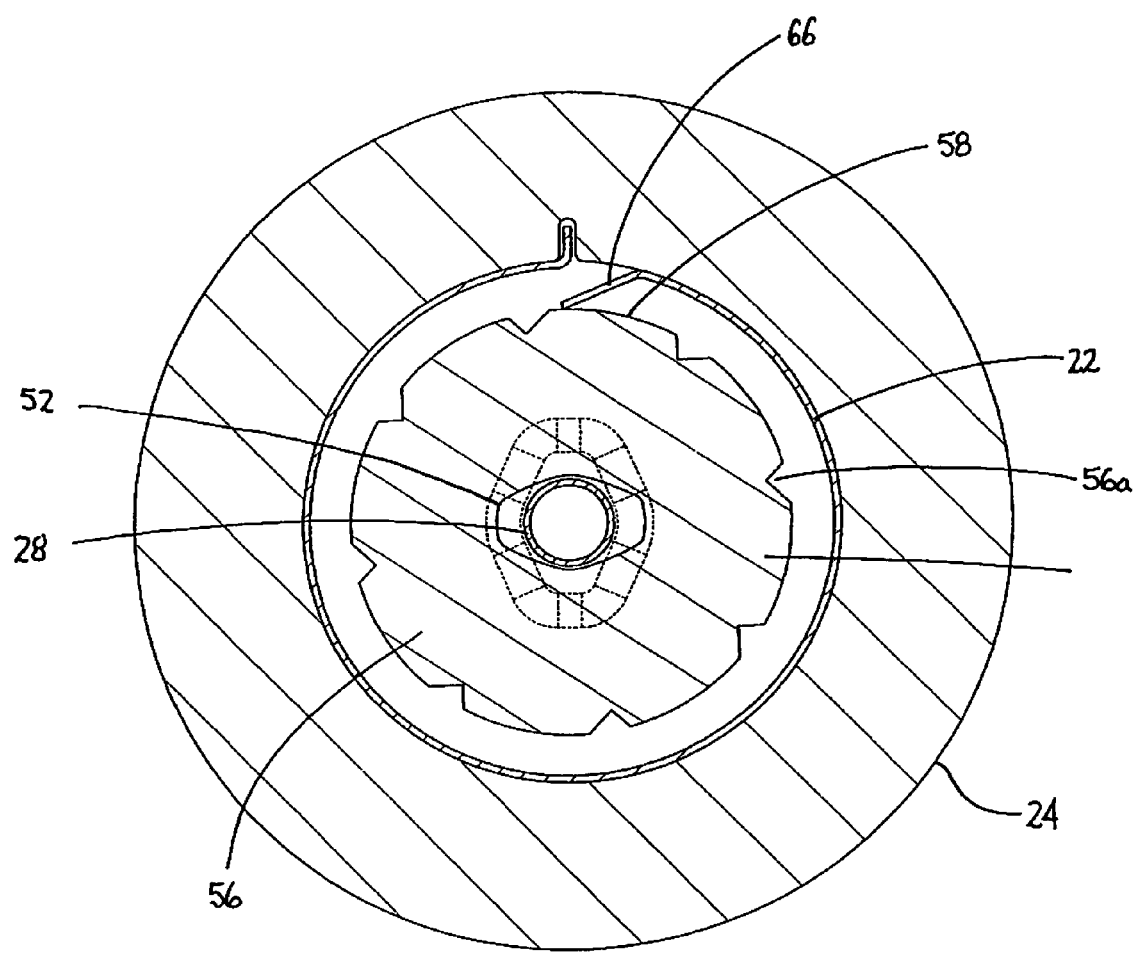
FIG. 17 is a cross-sectional view taken along section lines 17-17 of FIG. 16.

Referring to FIGS. 16 and 17, when device 10 is assembled, needle 28 is positioned through stepped bore 34 of housing 24, through throughbore 52 of locking member 20, and through catheter 14 of catheter assembly 12. Non-circular portion 72 of needle 28 is positioned within throughbore 52 of locking member 20 and locking member 20 is rotatably supported within central portion 38 of bore 34 of housing 24. Needle hub 30 is positioned adjacent a proximal end of housing 24. As illustrated in FIG. 17, stop member 66 of locking clip 22 is positioned on circular track 58. As discussed above, locking clip 22 is formed of a spring material such that stop member 66 is urged against circular track 58. Further, catheter hub 16 is positioned within distal portion 36 of stepped bore 34 such that annular rib 42 is positioned within an annular recess 76 formed in catheter hub 16 to releasably secure catheter hub 16 to housing 24. The distal end of housing 24 is formed of a material, e.g., plastic, having a degree of resiliency to facilitate disengagement of catheter hub 16 from housing 24. The distal end of catheter hub 16 may include a grasping surface configured to further facilitate disengagement of catheter hub 16 from housing 24. Alternatively, catheter hub 16 and housing 24 may contain other releasably securing structures such as bayonet, press-fit, or any other suitable engagement structure for releasably securing catheter hub 16 to housing 24.

Figure 19A:
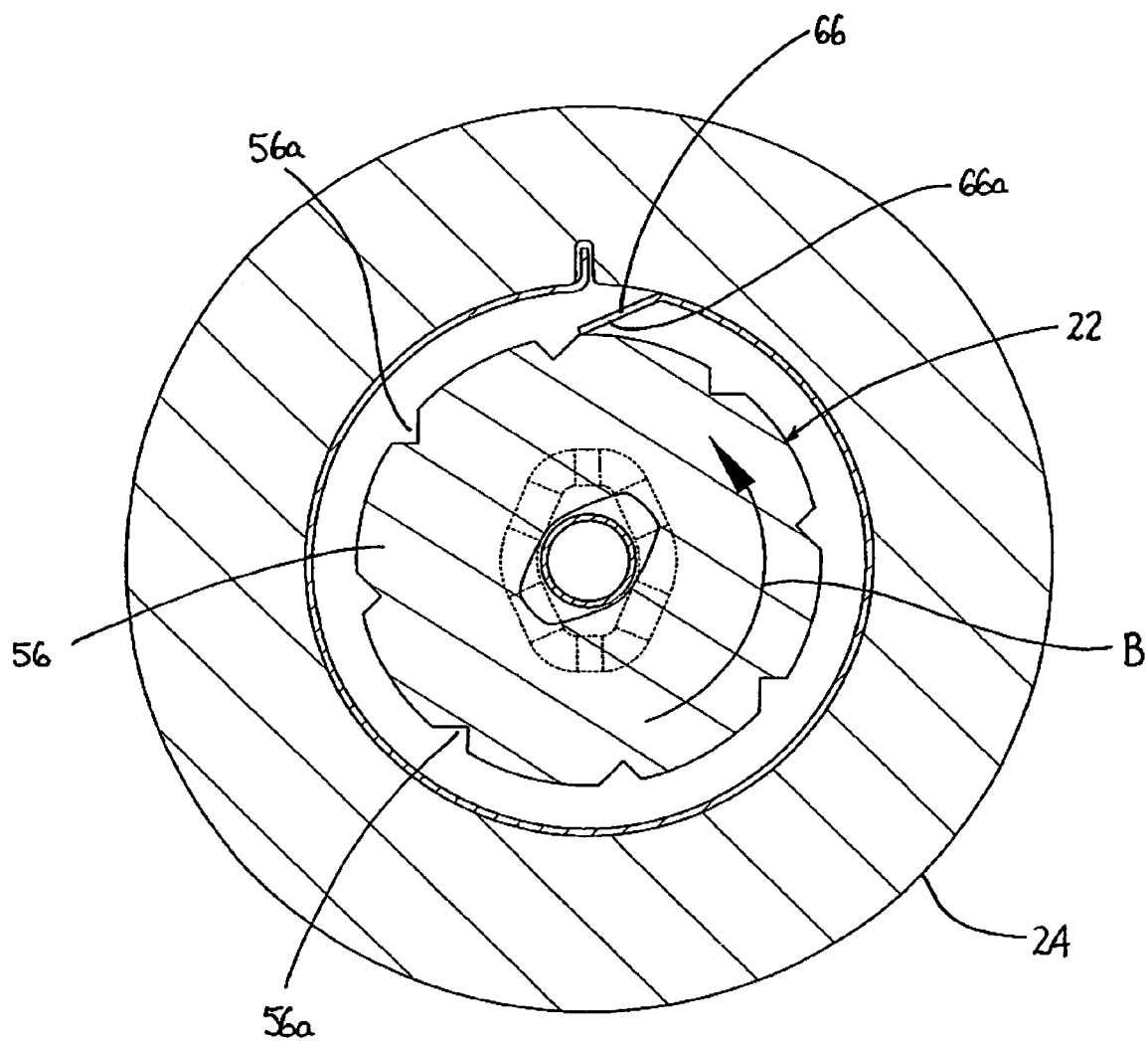
FIG. 19A is a cross-sectional view taken along section 19A-19A of FIG. 18.

Referring to FIGS. 18, 19 and 19A, when hub 30 is pulled in the direction indicated by arrow "A" in FIG. 18, needle 28 is withdrawn through cannula 14 and first non-circular portion 72 and then non-circular portion 70 pass through throughbore 52 of locking member 20. Since throughbore 52 has a non-circular bore which twists or rotates about the longitudinal axis to define a screw-like channel, as needle 28 is pulled proximally, locking member 20 is forced to rotate about the longitudinal axis in the direction indicated by arrow "B". As locking member 20 rotates, stop member 66 on locking clip 22 moves along circular track 58 and ratchets into and out of cutouts 56a (FIG. 19A). As discussed above, sloped surface 66a of stop member 66 allows rotation of locking member 20 in the direction indicated by arrow "B" but prevents rotation of locking member 20 in an opposite direction. It is noted that when non-circular portion 72 of needle 28 enters non-circular throughbore 48, needle 28 is prevented from rotating in relation to housing 24.

Figure 20:
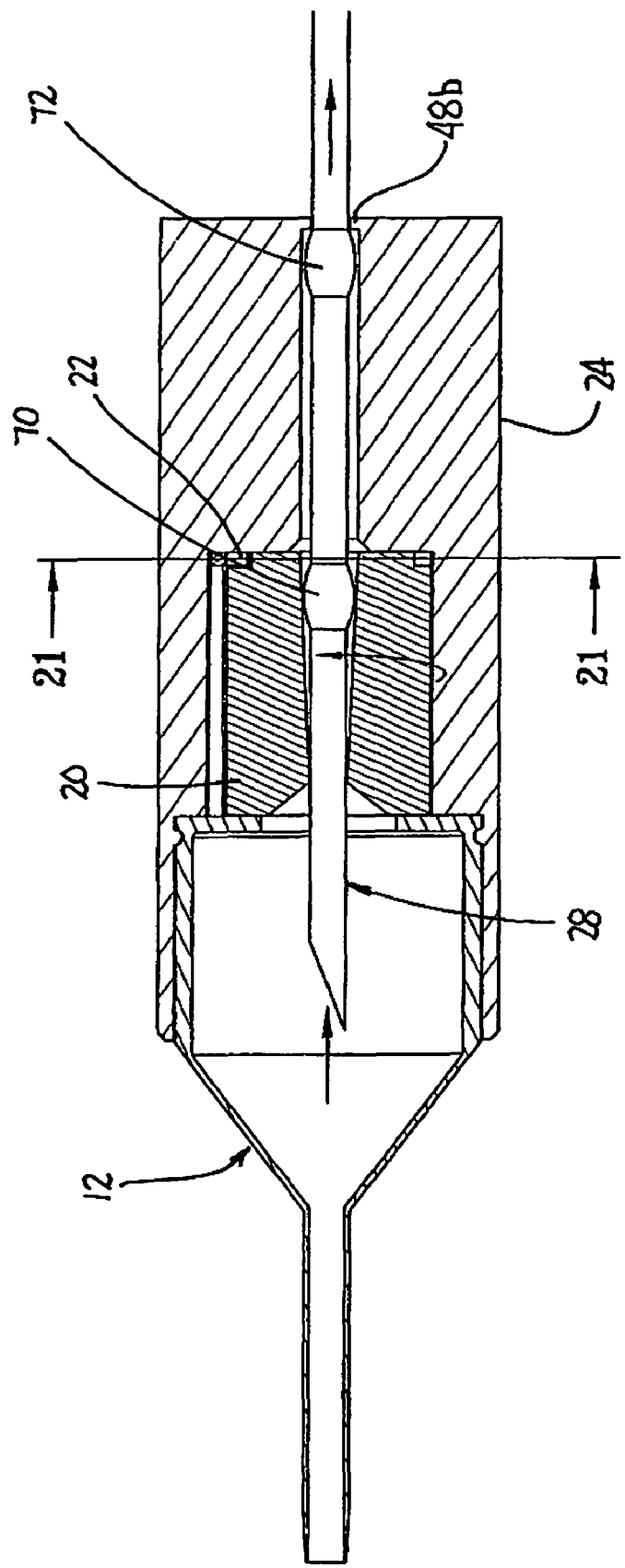
FIG. 20 is a side cross-sectional view of the I.V. catheter assembly and needle safety device shown in FIG. 18 with the needle fully retracted.
Figure 21:
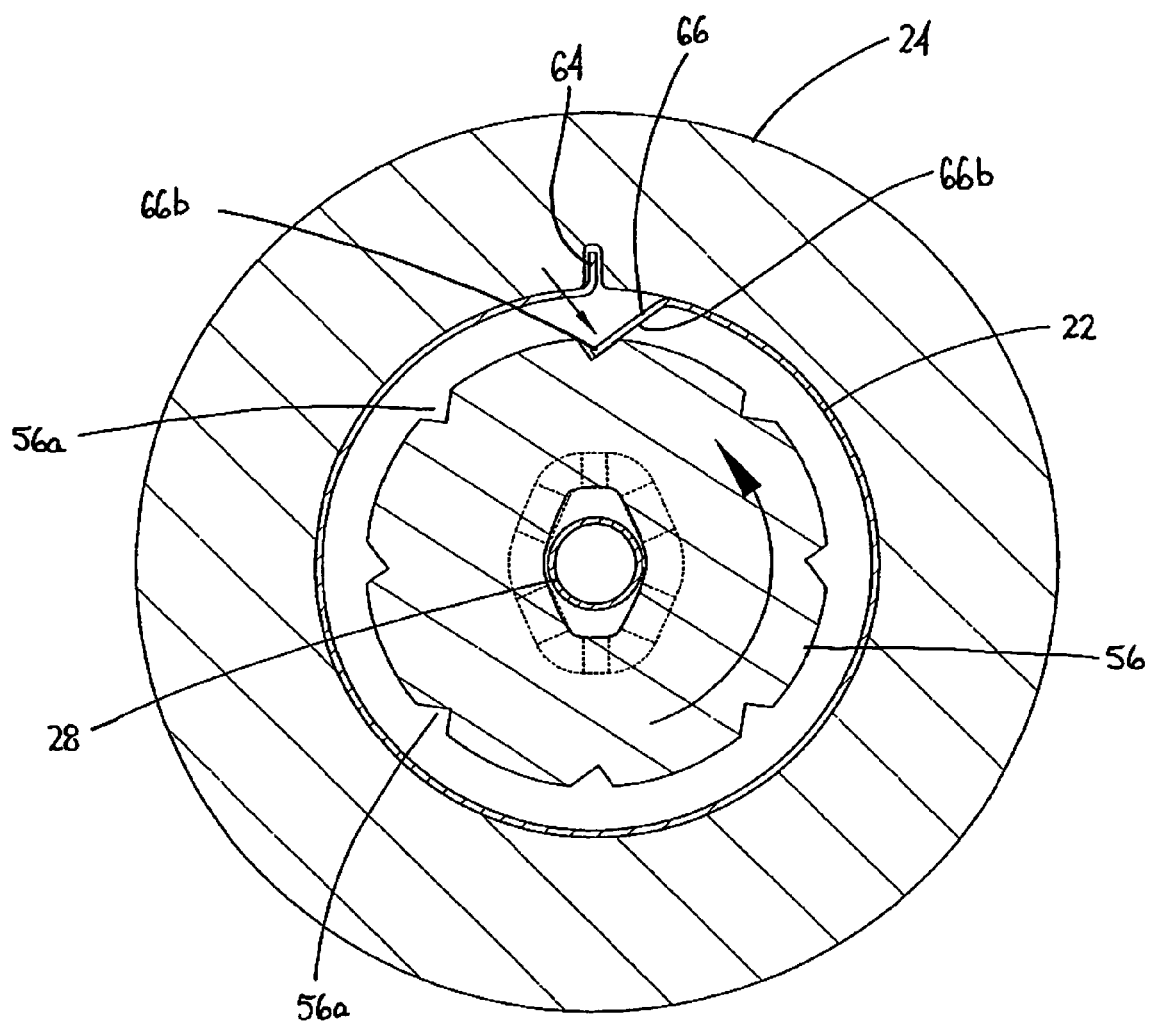
FIG. 21 is a cross-sectional view taken along section lines 21-21 of FIG. 20.

Referring to FIGS. 20 and 21, when needle 28 is retracted to the point non-circular portion 72 engages flange 48b, needle 28 is prevented from further proximal movement. Further, if an attempt is made to advance needle 28, tip 66b of stop member 66 of locking clip 22, if not already engaged in a cutout 56a, moves into engagement with a cutout 56a, to prevent rotation of locking member 20 (FIG. 21). When this occurs, advancement of needle 28 is prevented because of the screw-like configuration of throughbore 52.

Figure 22:
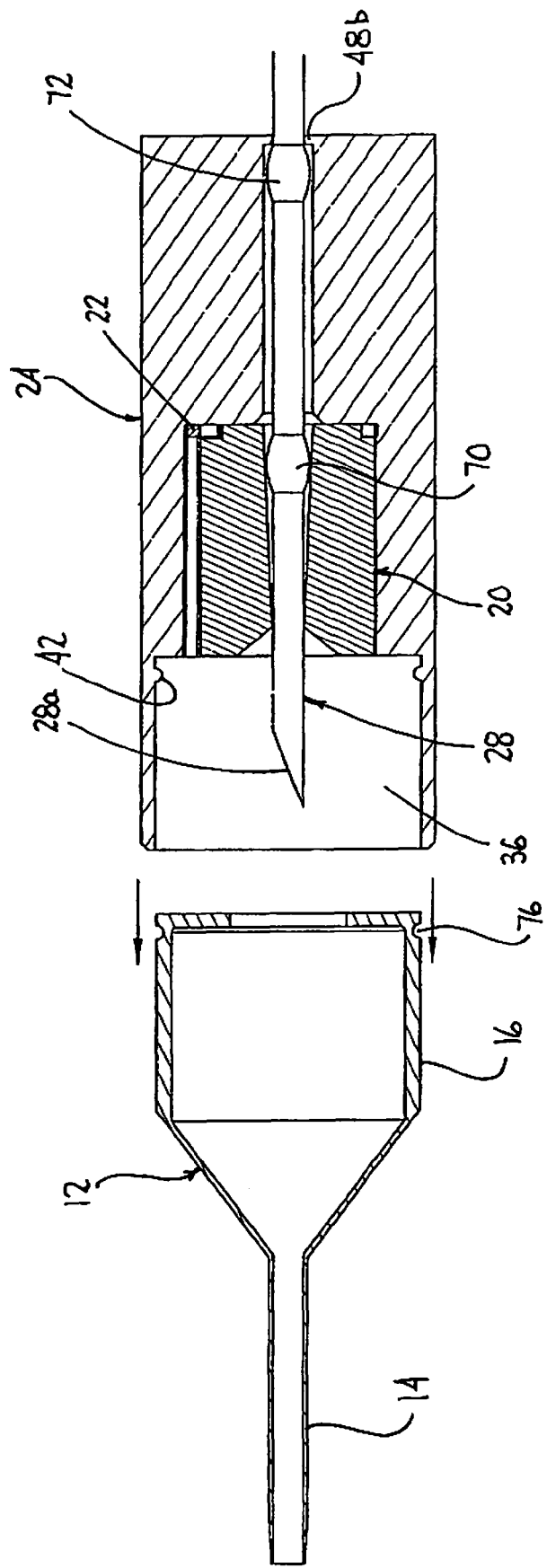
FIG. 22 is a side cross-sectional view of the I.V. catheter assembly and needle safety device shown in FIG. 20 with the catheter assembly separated from the lock assembly.

Referring to FIG. 22, as illustrated, when needle 28 is in its locked, retracted position, sharpened tip 28a of needle 28 is safely confined within distal portion 36 of stepped bore 34. As discussed above, flange 48b prevents proximal movement of needle 28 in relation to housing 24 of lock assembly 18 and since locking member 20 is prevented from rotating by locking clip 22, needle 28 cannot be moved distally in relation to housing 24. Thus, distal end 28a of needle 28 is safely confined within distal portion 36 of stepped bore 34 of housing 24.

Figure 23:
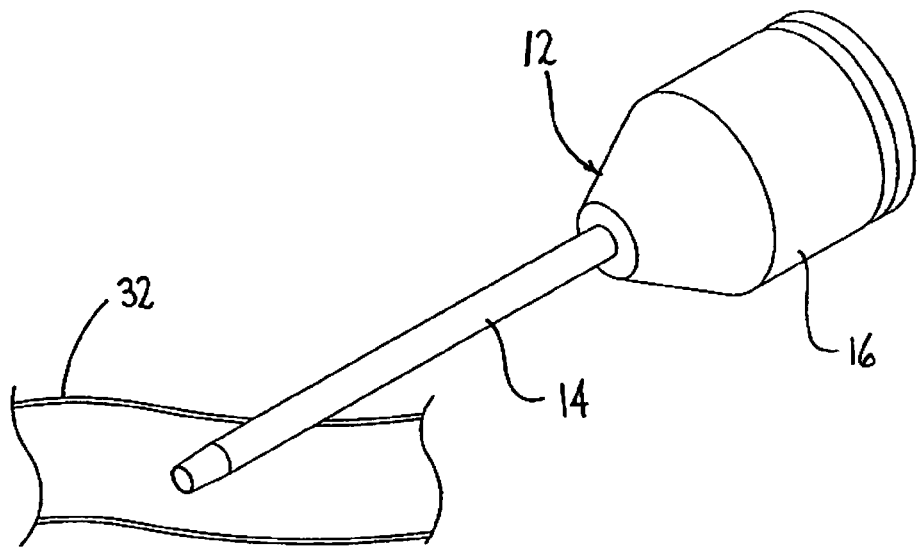
FIG. 23 is a side perspective view illustrating the catheter of the I.V. catheter assembly and needle safety device positioned within a vein.
Figure 24:
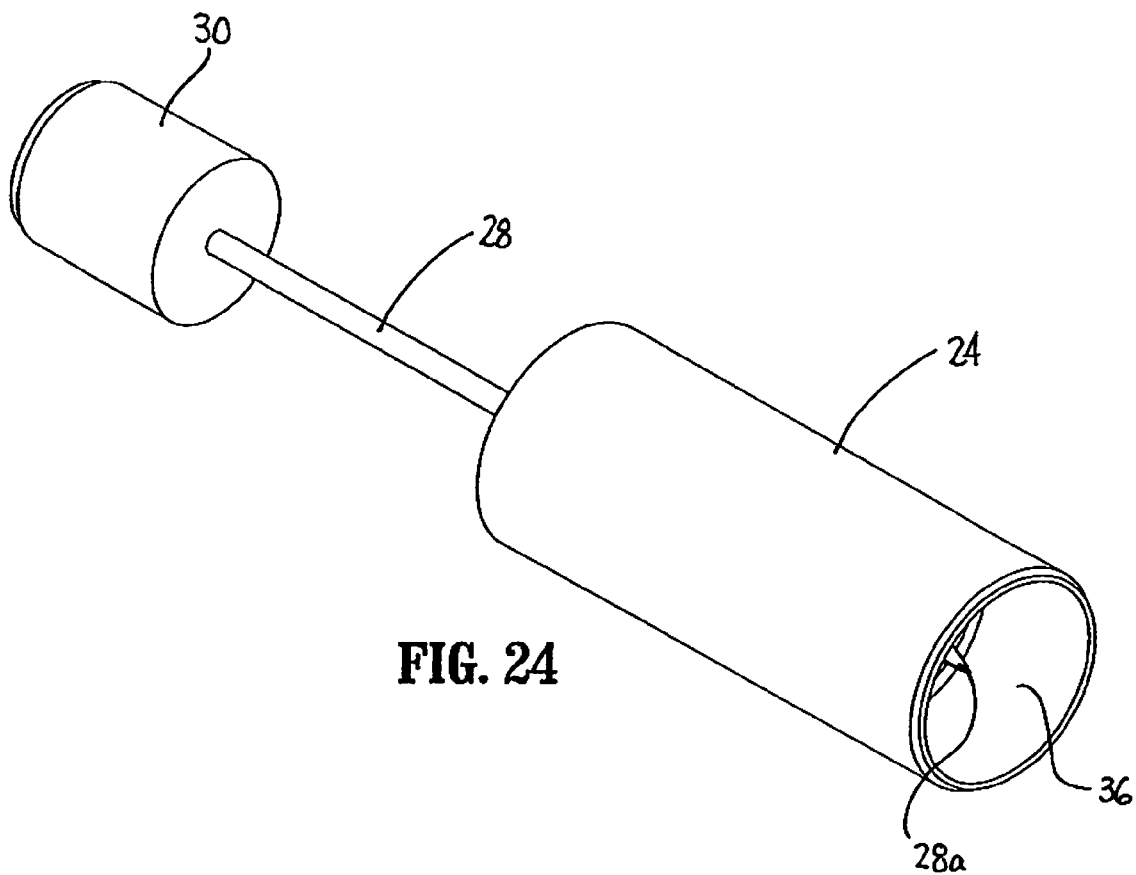
FIG. 24 is a side perspective view of the needle assembly and lock assembly of the I.V. catheter and needle safety device shown in FIG. 22 with the needle locked in its retracted position.

At this time, housing 24 with needle 28 locked therein (FIG. 24) can be separated from catheter assembly 12 (FIG. 23) by pulling catheter assembly 12 apart from housing 24 in the direction indicated by arrow "C" to disengage annular rib 42 of housing 24 from annular recess 76 of catheter hub 16. Lock assembly 18 and needle assembly 26 can now be safely disposed of by medical personnel.

FIGS. 25-35 illustrate another embodiment of the presently disclosed I.V. catheter assembly and needle safety device shown generally as 100. I.V. catheter assembly and needle safety device 100 includes a catheter assembly 112, a safety device or lock assembly 118 and a needle assembly 126. Catheter assembly 112 includes a catheter 114 and a catheter hub 116 supported on a proximal end of catheter 114. Safety device or lock assembly 118 includes a rotatable locking member 120, a locking clip 122 and a lock housing 124. Needle assembly 126 includes an elongated needle 128 and a needle hub 130. As will be discussed in further detail below, needle 128 is positioned through lock assembly 118 and catheter assembly 112 such that in its extended position, a sharpened tip 128a of needle 128 extends from the distal end of catheter 114. As is known in the art, sharpened tip 128a facilitates insertion of needle 128 and catheter 114 into vasculature, e.g., vein 132 (FIG. 25), of a patient.

Figures 25, 26:
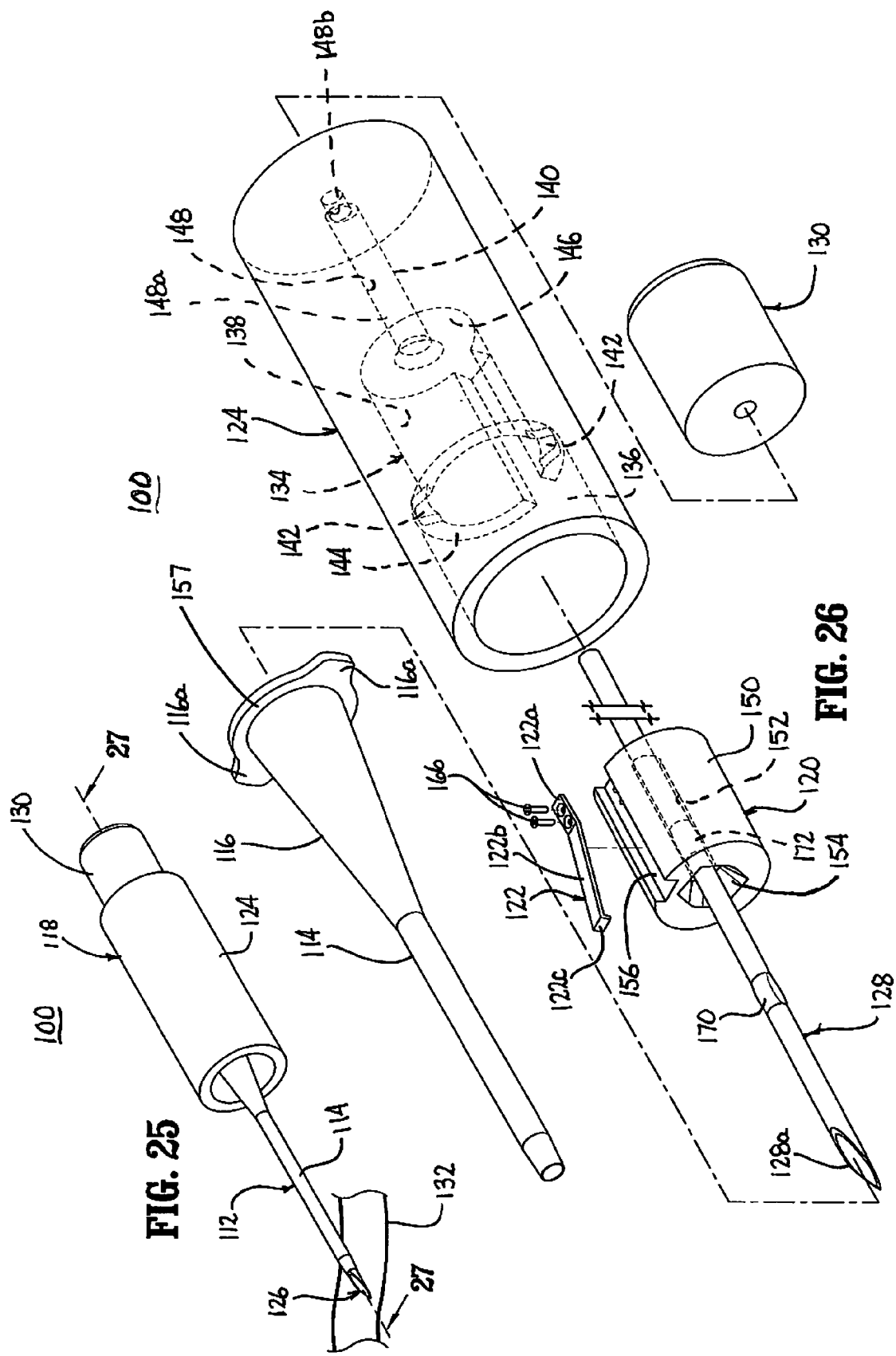
FIG. 25 is a side perspective view of another embodiment of the presently disclosed I.V. catheter assembly and needle safety device with the needle tip of the needle projecting from the distal end of the catheter and the catheter inserted into a vein.
FIG. 26 is a side perspective view of the I.V. catheter assembly and needle safety device shown in FIG. 25 with parts separated.
Figure 27:
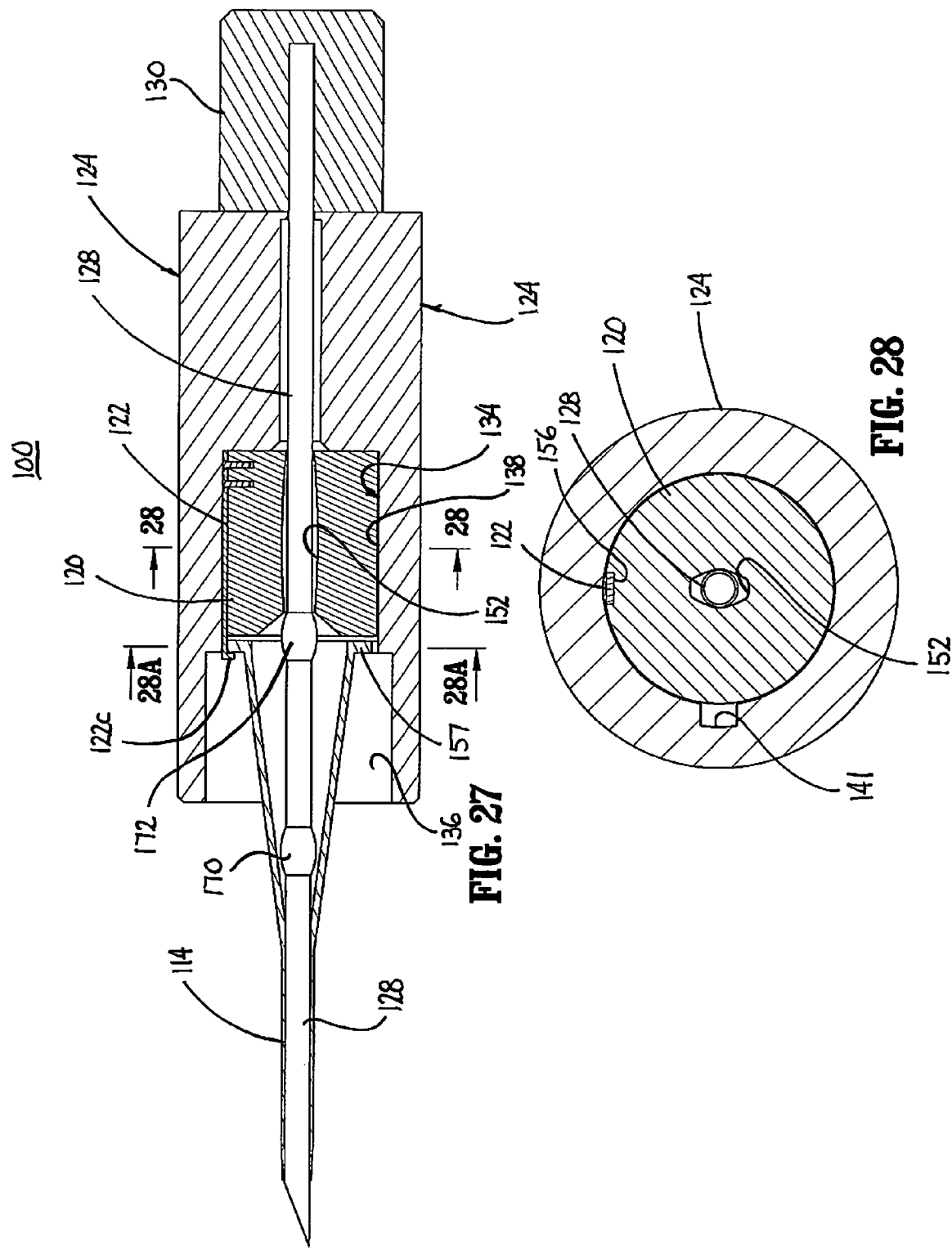
FIG. 27 is a cross-sectional view of the presently disclosed I.V. catheter assembly and needle safety device taken along section lines 27-27 of FIG. 25.

Referring to FIGS. 26 and 27, lock housing 124 defines a stepped bore 134 having a substantially cylindrical distal portion 136, a substantially cylindrical central portion 138 and a proximal portion 140. Distal portion 136 is dimensioned to receive the proximal end of catheter hub 116. A first shoulder portion or step 144 is positioned between distal portion 136 and central portion 138 of stepped bore 134. Step 144 includes a pair of cutouts 142 which are configured to receive projections or ears 116a formed on the proximal end of catheter hub 116 when catheter assembly 112 is secured to housing 124 (FIG. 16). The receipt of projections 116a in cutouts 142 prevents rotation of hub 116 in relation to lock housing 124 as will be discussed in further detail below. Central portion 138 of stepped bore 134 is dimensioned to rotatably receive locking member 120 of lock assembly 118 and defines a longitudinal channel 141. A second shoulder portion or step 146 is positioned between central portion 138 and proximal portion 140 of stepped bore 134. Step 146 engages the proximal end of locking member 120 when member 120 is positioned in central portion 138 of bore 134. Proximal portion 140 includes a throughbore 148. At least a portion 148a of throughbore 148 has a non-circular shape, e.g., truncated oval shape. The proximal end of throughbore 148 also includes an inwardly extending flange 148b of reduced diameter which will be discussed in further detail below. Non-circular portion 148a functions to prevent rotation of needle 128 in relation to housing 124 and to lock needle 128 in a retracted position in relation to housing 124 as will be described in detail below.

Figure 28:
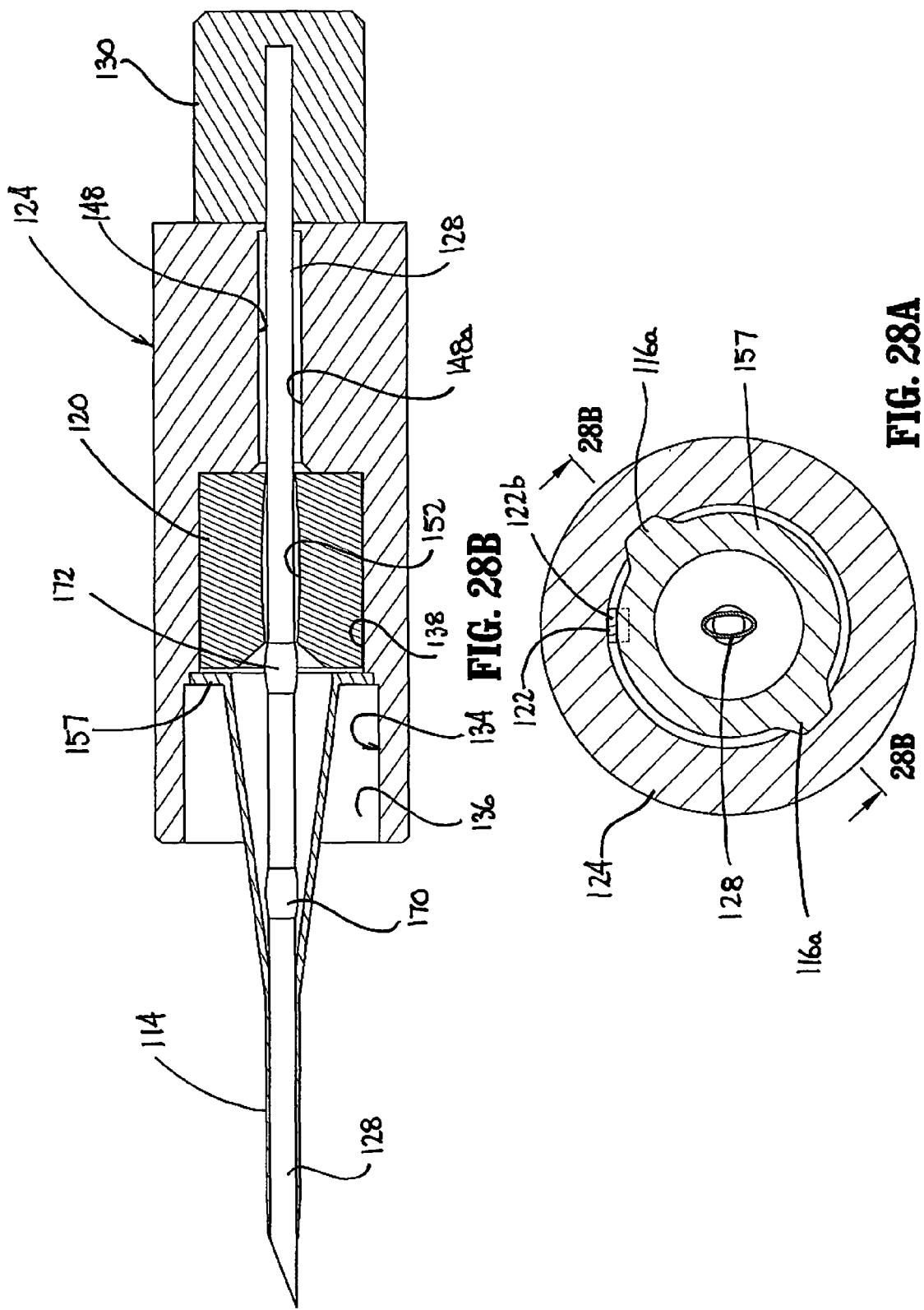
FIG. 28 is a cross-sectional view of the presently disclosed I.V. catheter assembly and needle safety device taken along section lines 28-28 of FIG. 27.

Referring to FIGS. 26-28, locking member 120 has a substantially cylindrical body 150 defining a non-circular throughbore 152, e.g., truncated oval shape, which is rotated or twisted along its longitudinal axis, e.g. partial helix, in the manner described above with respect to throughbore 52 of locking member 20. A distal end 150a of locking member 120 includes a channeling surface 154 which will be discussed in further detail below. A longitudinally extending channel 156 is formed along an outer surface of rotatable locking member 120. Locking clip 22 is supported within channel 156 and includes a base portion 122a, an angled resilient portion 122b which extends outwardly from base portion 122a, and a retaining portion 122c which extends downwardly from resilient portion 122b. As illustrated, base portion 122a is secured within channel 156 with at least one screw 166 such that angled resilient portion 122b extends outwardly of channel 156 in its undeformed state. When rotatable lock member 120 is positioned within central portion 138 of stepped bore 134, angled resilient portion 122b of locking clip 122 is urged to a deformed state by an inner wall of lock housing 124. In the deformed state, locking clip 122 is positioned within channel 156 of rotatable locking member 120 such that locking member 120 can freely rotate within central portion 138 of stepped bore 134. See FIG. 28. When locking member 120 is rotated to a position in which locking clip 122 is aligned with longitudinal channel 141 of lock housing 124, angled resilient portion 122b will return to its non-deformed state and move into longitudinal channel 141 and obstruct further rotation of locking member 120 within central portion 138 of stepped bore 134. See FIG. 32.

As illustrated in FIG. 27, when locking clip 122 is in the deformed state within channel 156, retaining portion 122c engages a top surface of a proximal rim 157 of hub 116 to releasably retain catheter assembly 112 within distal portion 136 of stepped bore 134. When locking clip 122 rotates to a position aligned with longitudinal channel 141 and returns to the non-deformed state, angled resilient portion 122b springs outwardly to disengage retaining portion 122c from rim 157 of hub 116 to release catheter assembly 112 from within distal portion 136 of stepped bore 134. See FIG. 31.

Referring to FIGS. 25-27, as discussed above, needle assembly 126 includes a needle hub 130 and a needle 128 having a sharpened tip 128a. Sharpened tip 28a defines a beveled surface configured to pierce body tissue to access vasculature of a patient. Needle 130 further includes first and second non-circular portions 170 and 172 which are configured and dimensioned to be slidably received within throughbore 152 of locking member 120 and within non-circular portion 148a of throughbore 148 of housing 124. Needle hub 130 is secured to the proximal end of needle 128 and provides a gripping surface to facilitate removal of needle 128 from catheter assembly 112. Needle hub 130 can be secured to needle 128 using any known fastening technique including adhesion, crimping, press-fitting.

Referring to FIGS. 27-28A, when device 110 is assembled, needle 128 is positioned through stepped bore 134 of housing 124, through throughbore 152 of locking member 120, and through catheter 114 of catheter assembly 112. Non-circular portion 172 of needle 128 is positioned within throughbore 152 of locking member 120 and locking member 120 is rotatably supported within central portion 138 of bore 134 of housing 124. Needle hub 130 is positioned adjacent a proximal end of housing 124. As illustrated in FIGS. 27 and 28, locking clip 122 is positioned within channel 156 of rotatable member 120 such that retaining portion 122c is engaged with rim 157 of catheter assembly 112 to releasably secure catheter assembly 112 within distal portion 136 of lock housing 124. As discussed above, locking clip 22 is formed of a spring material such that angled resilient portion 122c is urged outwardly against an inner wall of housing 124.

Referring to FIGS. 29 and 30, when hub 130 is pulled in the direction indicated by arrow "D" in FIG. 29, needle 128 is withdrawn through cannula 114 such that first non-circular portion 172 and then second non-circular portion 170 pass through throughbore 152 of locking member 120. Since throughbore 152 has a non-circular bore which twists or rotates about the longitudinal axis to define a screw-like channel, as needle 128 is pulled proximally, locking member 120 is forced to rotate about the longitudinal axis in the direction indicated by arrow "E". As locking member 120 rotates, locking clip 122 moves in the direction indicated by arrow "F" from a position angularly offset, e.g. 90°, from longitudinal channel 141 of lock housing 124 towards a position aligned with longitudinal channel 141. Engagement between projections 116a and cutouts 142 prevent hub assembly from rotating with locking member 120.

Referring to FIGS. 31 and 32, when needle assembly 126 is retracted to a position to rotate rotatable locking member 120 to a position in which locking clip 122 is aligned with longitudinal channel 141, angled resilient portion 122b springs outwardly into longitudinal channel 141. When this occurs, retaining portion 122c disengages from rim 157 of catheter assembly 112 to release catheter assembly 112 from distal portion 136 of lock housing 124. See FIG. 33. In this position, sharpened tip 128a of needle 128 is positioned within distal portion 136 of lock housing 124. Further, since locking clip 122 is positioned within longitudinal channel 141 of lock housing 124, rotatable locking member 120 is prevented from rotating. Thus, needle 128 cannot be advanced or retracted in relation to lock housing 124 because of screw-like configuration of throughbore 152 and sharpened tip 128a of needle 128 is safely retained within lock housing 124. Needle 128 also cannot be retracted from lock housing 124 because flange 148b obstructs movement of non-circular portion 172 of needle 128.

Figure 33:
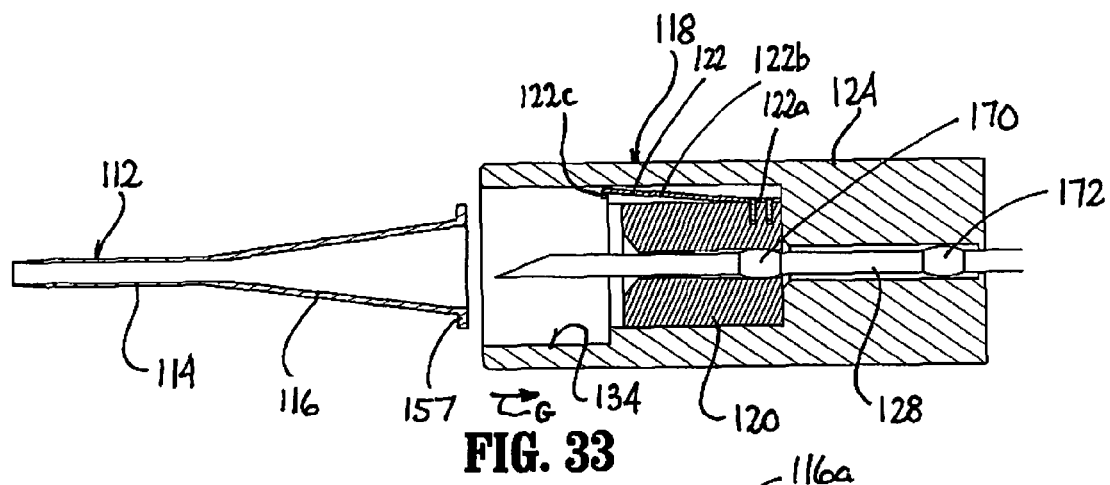
FIG. 33 is a side cross-sectional view of the I.V. catheter assembly and needle safety device shown in FIG. 31 with the catheter and catheter hub separated from the lock housing.
Figure 34:
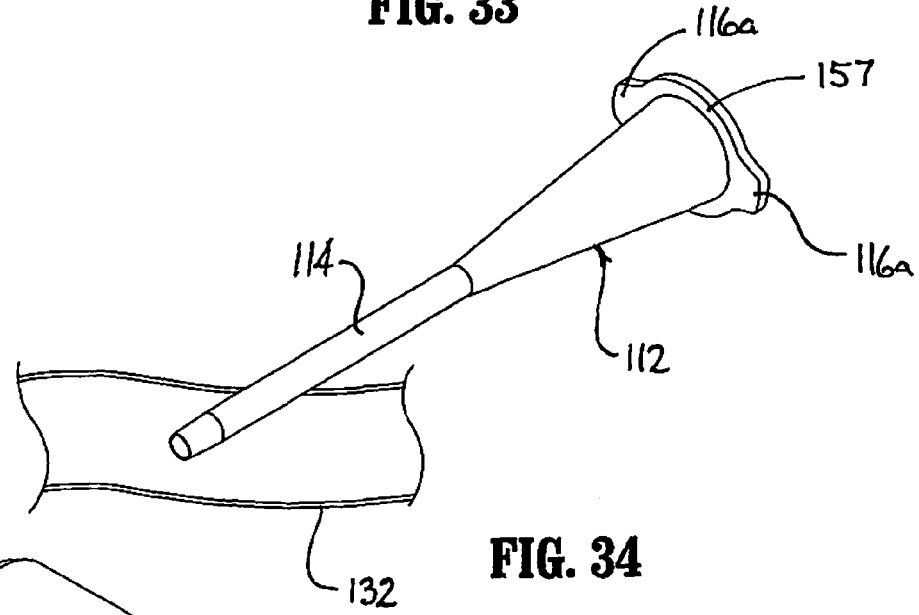
FIG. 34 is a side perspective view of the catheter of the presently disclosed I.V. catheter assembly shown in FIG. 31 positioned within a vein.
Figure 35:
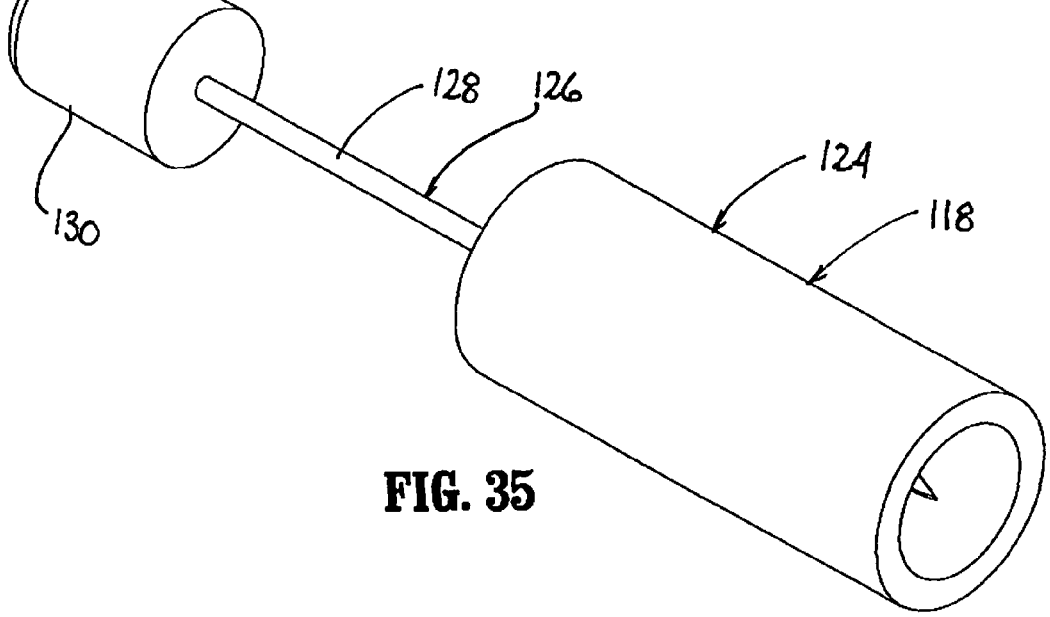
FIG. 35 is a side perspective view of the needle assembly and lock assembly of the I.V. catheter and needle safety device shown in FIG. 31 with the needle locked in its retracted position.

At this time, housing 124 with needle 128 locked therein (FIG. 33) can be separated from catheter assembly 112 (FIG. 34) by pulling housing 124 apart from catheter assembly 112 in the direction indicated by arrow "G" in FIG. 33. Lock assembly 118 and needle assembly 126 can now be safely disposed of by medical personnel.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An I.V. catheter assembly and needle safety device comprising:
a catheter assembly including a catheter and a catheter hub;
a lock assembly including a housing, a locking member and a resilient locking clip, the housing defining a throughbore and having a distal end configured to engage a proximal end of the catheter hub, the locking member defining a throughbore and being rotatably supported within the housing throughbore, the housing throughbore defining a longitudinal channel, which is sized to accommodate the resilient locking clip, wherein the resilient locking clip is supported on the locking member, the resilient locking clip being rotatable with the locking member from a first position misaligned with the longitudinal channel to a second position aligned with the longitudinal channel to substantially prevent rotation of the locking member with respect to the housing; and
a needle having a distal tip, the needle being positioned through the housing throughbore, the locking member throughbore and the catheter in an advanced position such that the distal tip of the needle projects from a distal end of the catheter, the needle being movable from the advanced position to a retracted position, wherein the distal tip of the needle is positioned within the housing, the needle having a first portion movable through the locking member throughbore, the first portion being configured to effect rotation of the locking member with respect to the housing as the needle is moved linearly through the locking member throughbore.

2. The device according to claim 1, wherein the distal tip of the needle is sharpened.

3. The device according to claim 1, wherein the resilient locking clip is configured to releasably engage the proximal end of the catheter hub.

4. The device according to claim 1, wherein the first portion of the needle includes a non-circular portion.

5. The device according to claim 4, wherein the locking member throughbore has a non-circular shape which rotates about its longitudinal axis such that the locking member throughbore receives the first portion of the needle in a screw-like manner.

6. The device according to claim 5, wherein the needle includes a pair of spaced non-circular portions.

7. The device according to claim 1, wherein the locking member defines a channel, the locking clip being secured within the channel.

8. The device according to claim 7, wherein the locking clip includes an angled resilient portion which projects outwardly from the locking member channel in an undeformed state.

9. The device according to claim 8, wherein the locking member is substantially cylindrical and is rotatably supported within the housing throughbore.

* * * * *